(12) United States Patent
Simpson et al.

(10) Patent No.: US 8,489,427 B2
(45) Date of Patent: Jul. 16, 2013

(54) WIRELESS MEDICAL DATA COMMUNICATION SYSTEM AND METHOD

(75) Inventors: Thomas L. C. Simpson, Burlington, WI (US); Laura M. Letellier, Buffalo Grove, IL (US); James P. Martucci, Libertyville, IL (US)

(73) Assignee: Baxter International Inc., Deerfield, IL (US)

( * ) Notice: Subject to any disclaimer, the term of this patent is extended or adjusted under 35 U.S.C. 154(b) by 1628 days.

(21) Appl. No.: 10/659,760

(22) Filed: Sep. 10, 2003

(65) Prior Publication Data

US 2004/0121767 A1    Jun. 24, 2004

Related U.S. Application Data

(63) Continuation-in-part of application No. 10/059,929, filed on Jan. 29, 2002, and a continuation-in-part of application No. 10/135,180, filed on Apr. 30, 2002, now abandoned, and a continuation-in-part of application No. 10/424,553, filed on Apr. 28, 2003, now Pat. No. 7,698,156.

(60) Provisional application No. 60/444,350, filed on Feb. 1, 2003, provisional application No. 60/488,273, filed on Jul. 18, 2003, provisional application No. 60/528,106, filed on Dec. 8, 2003.

(51) Int. Cl.
*G06Q 10/00* (2012.01)

(52) U.S. Cl.
USPC .................................................. 705/3; 705/2

(58) Field of Classification Search
USPC ............................................................. 705/3
See application file for complete search history.

(56) References Cited

U.S. PATENT DOCUMENTS

| | | | |
|---|---|---|---|
| 5,401,059 A | 3/1995 | Ferrario | |
| 5,781,442 A | 7/1998 | Engleson et al. | |
| 5,827,180 A * | 10/1998 | Goodman | 600/300 |
| 6,406,426 B1 * | 6/2002 | Reuss et al. | 600/300 |
| 6,564,104 B2 * | 5/2003 | Nelson et al. | 607/60 |
| 6,641,533 B2 * | 11/2003 | Causey et al. | 600/300 |
| 6,795,421 B1 * | 9/2004 | Heinonen et al. | 370/338 |
| 7,512,424 B2 * | 3/2009 | Hossain et al. | 455/574 |
| 2002/0038392 A1 * | 3/2002 | De La Huerga | 710/8 |
| 2004/0158193 A1 * | 8/2004 | Bui et al. | 604/65 |
| 2004/0204673 A1 * | 10/2004 | Flaherty | 604/65 |

FOREIGN PATENT DOCUMENTS

| | | |
|---|---|---|
| JP | 2-111375 | 4/1990 |
| JP | 11-505352 | 5/1995 |
| JP | 11-505352 | 5/1999 |
| JP | 2004-519020 | 6/2004 |
| WO | 96/36923 | 11/1996 |
| WO | 01/88828 A2 | 11/2001 |
| WO | 2001-088828 | 11/2011 |

OTHER PUBLICATIONS

Extended European Search Report and Written Opinion for European Application No. 10075379.7 mailed Dec. 8, 2010.
Japanese Office Action issued May 8, 2012, for corresponding Japanese Appln. No. 2011-19579.

(Continued)

*Primary Examiner* — Hiep V Nguyen
(74) *Attorney, Agent, or Firm* — K&L Gates LLP

(57) ABSTRACT

A system and method is disclosed for indicating the loss of a wireless communication link within a healthcare facility.

46 Claims, 10 Drawing Sheets

OTHER PUBLICATIONS

Japanese Office Action issued Nov. 26, 2012, for corresponding Japanese Appln. No. 2008-270389.

Japanese Office Action for Application No. 2011-289835 dated Apr. 12, 2013.

* cited by examiner

WIRELESS MEDICAL DATA COMMUNICATION SYSTEM AND METHOD

CROSS-REFERENCE TO RELATED APPLICATIONS

This application is a continuation-in-part, and as such claims priority from and expressly incorporates by reference and makes a part hereof, the following co-pending U.S. utility patent applications entitled: "System and Method for Operating Medical Devices," having Ser. No. 10/059,929 and being filed on Jan. 29, 2002 and published on Jul. 31, 2003 under Publication No. US-2003-0141981-A1; "Medical Treatment Verification System and Method," having Ser. No. 10/135,180 and filed on Apr. 30, 2002; and, "System and Method for Identifying Data Streams Associated with Medical Equipment," having Ser. No. 10/424,553 and filed on Apr. 28, 2003; and the following U.S. provisional patent applications entitled: "Messaging Apparatus and Method," having Ser. No. 60/444,350 and filed on Feb. 1, 2003; "Wireless Medical Data Communication System and Method," having Ser. No. 60/488,273 and filed on Jul. 18, 2003; and, "Wireless Data Communication System and Method," having Ser. No. 60/528,106 and filed on Dec. 8, 2003.

TECHNICAL FIELD

This invention relates generally to wireless medical data communication systems and methods. More particularly, the present invention relates to a system and method for reporting on the integrity of a wireless communication link.

BACKGROUND OF THE INVENTION

Patient care systems typically include computer networks, medical devices for treating a patient, and controls for the medical devices. Although patient care systems have improved through the use of computerized automation systems and methods, patient care systems continue to rely heavily upon manual data management processes for medical devices and controls for medical devices. For example, nursing stations are typically connected to the computer networks in modern hospitals, but it is unusual for the computer network to extend to a patient's room. Computer networks offer the opportunity for automated data management processing including the operating and monitoring of medical devices and controls for the medical devices at the point-of-care. Despite advances in the field, automated data management technology has been underutilized for point-of-care applications due to a lack of more efficient systems and methods. As dependance on automated technology grows, a need also grows in providing users with the ability to determine the operating status of system or subsystems.

SUMMARY OF THE INVENTION

The present invention provides a system and method for reporting on the integrity of a wireless communication link within a healthcare facility.

Generally, the present invention includes a system having a medication administration module and a wireless remote device located within a healthcare facility. The medication administration module is associated with the medication treatment application device, such as an infusion pump. The wireless remote device includes a message indicator, such as a visual display or an audible alarm, that is responsive to a status information output generated by the medication administration module and transmitted over a wireless communication link. The wireless remote device also includes a module or application for generating a time-out when the wireless communication link is lost.

Other systems, methods, features, and advantages of the present invention will be, or will become, apparent to one having ordinary skill in the art upon examination of the following drawings and detailed description. It is intended that all such additional systems, methods, features, and advantages included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
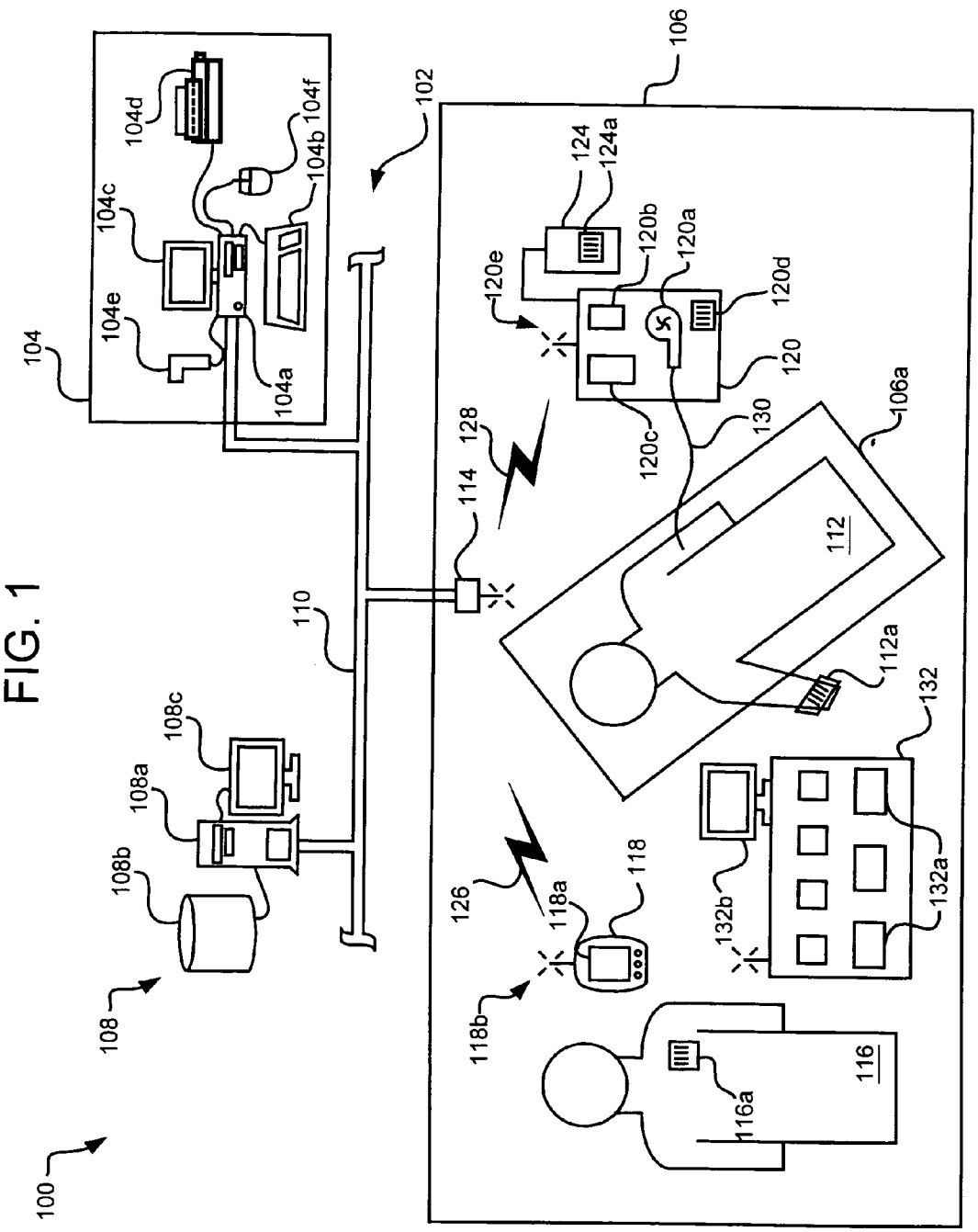
FIG. 1 is a simplified graphical representation of a patient care system. The patient care system includes a pharmacy computer, a central system, and a digital assistant at a treatment location.

While this invention is susceptible of embodiments in many different forms, there is shown in the drawings and will herein be described in detail a preferred embodiment of the invention. The present disclosure is to be considered as an exemplification of the principles of the invention and is not intended to limit the broad aspect of the invention to the embodiment illustrated.

Figure 2:
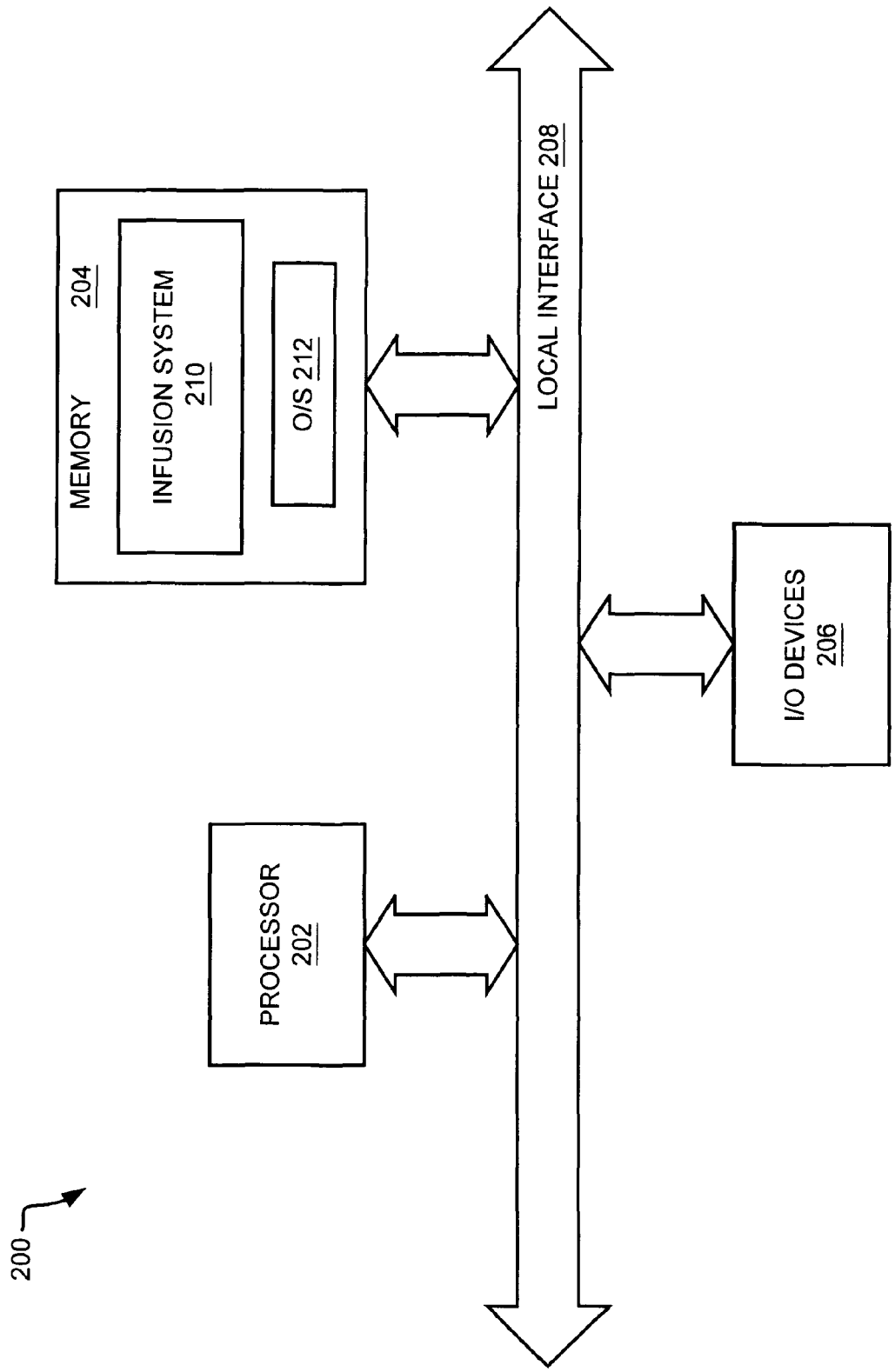
FIG. 2 is a block diagram of a computer system representative of the pharmacy computer, the central system, and/or the digital assistant of FIG. 1. The system includes an infusion system or a portion thereof.

FIG. 1 is a graphical representation of a patient care system. The patient care system 100 includes a pharmacy computer 104, a central system 108, and a treatment location 106, linked by a network 102. Patient care system 100 also includes an infusion system 210 (FIG. 2). Infusion system 210 is a medication system preferably implemented as a computer program, and in particular a module or application (i.e., a program or group of programs designed for end users), resident on one or more electronic computing devices within the patient care system 100. As described in detail further herein, the infusion system 210 links clinicians, such as physicians, pharmacists, and nurses, in an interdisciplinary approach to patient care.

Figure 3:
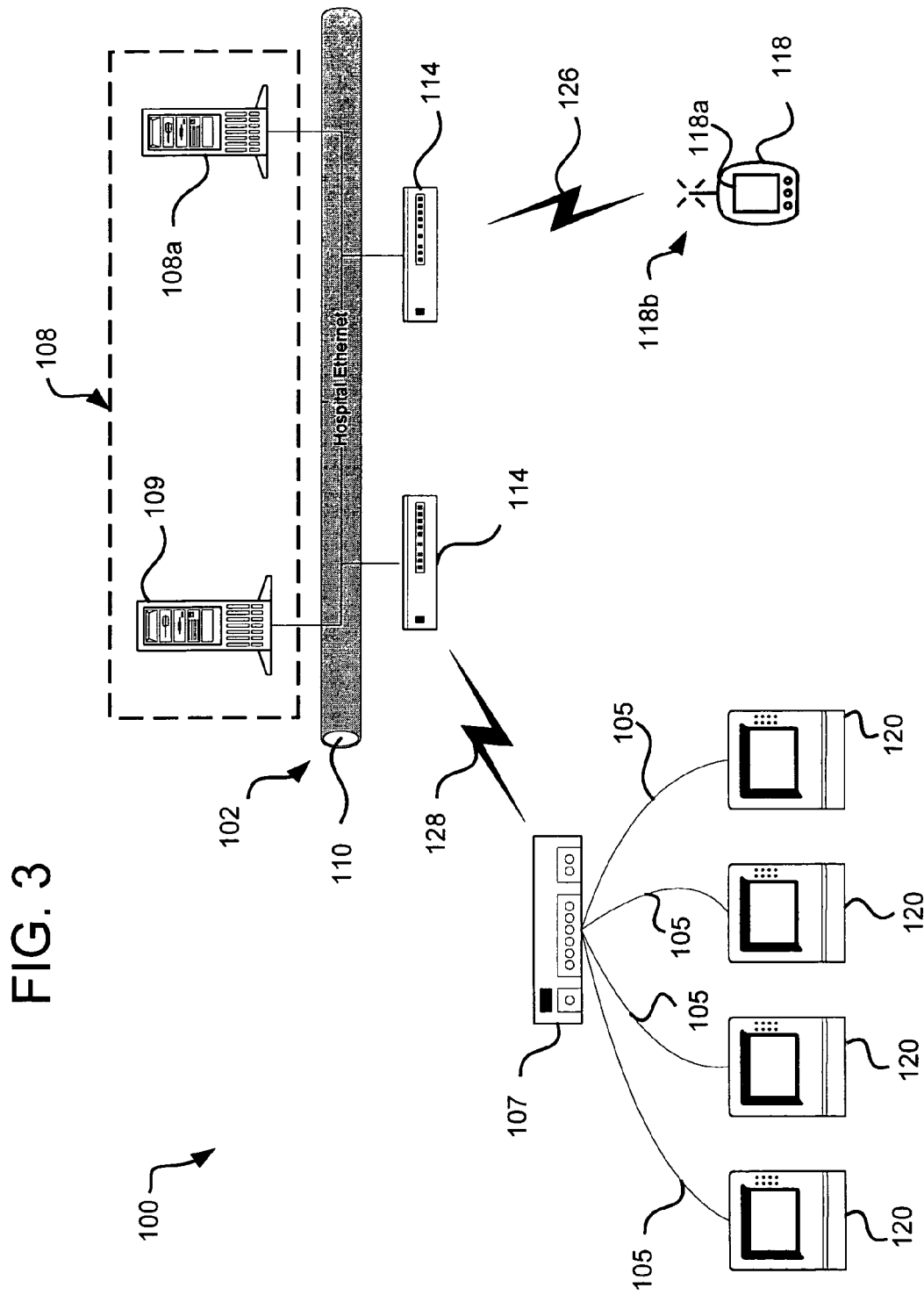
FIG. 3 is a simplified graphical representation of portions of the patient care system of FIG. 1.

Turning to FIG. 3, the patient care system 100 can include a plurality of infusion pumps 120 connected to a hub or interface 107. As explained in detail further herein, the infusion pumps 120 can be of conventional design wherein each infusion pump 120 is associated with a patient. However, as will be appreciated by those having ordinary skill in the art, the infusion pumps 120 shown in FIG. 3 do not have to be associated with the same patient or treatment location even though the infusion pumps are connected to the same hub 107. Moreover, each infusion pump 120 can be a single channel pump or a multiple channel pump, such as a triple channel pump.

In an embodiment, the serial port or other I/O port of the infusion pumps 120 are connected to the hub 107 using a conventional non-wireless transmission medium 105 such as twisted-pair wire, coaxial cable, fiber optic cable, or the like. Preferably, the hub 107 can connect to a plurality of infusion pumps 120 or just a single pump. The hub 107 provides for receiving signals from the connected pumps and regenerating the received signals. In particular, the received signals from the pumps 120 are converted by the hub 107 into a format suitable for transmission onto the system network 102 via wireless communication path or link 128 and cable communication system 110.

As shown in FIG. 3, a plurality of access points 114 within the healthcare facility provide an interface between the wireless communication paths and the cable communication system. Preferably, when the system network 102 is unavailable, the hub 107 stores the signals received from the pumps 102, and then transmits the converted signals to the system network 102 through the access point 114 once the system network becomes available. In a preferred embodiment, communication between the hub 107 and the access points 114 is unidirectional from the hub 107 to the access point 114 and ultimately the network 102. As such, in the present system the infusion pumps 120 can transmit data to the network 102, however, the network 102 cannot transmit data to the infusion pumps 120.

As shown in FIGS. 1 and 3, the central system 108 can include one or more servers. Preferably, but not necessarily, the central system 108 can include a server 109, shown in FIG. 3, for performing activities such as prescription comparisons, logging pump status, and forwarding alarms and alerts to clinicians as described in detail further herein. If required, the operations performed by the server 109 are compliant with the Health Insurance Portability Act of 1996 (August 21), Public Law 104-191. Typically, the data resident in server 109 is a subset of the data resident in the server 108a. As explained above, such data is generally that required for the functions or performance of the digital assistants 118 and infusion pumps 120. In one embodiment, a separate communication system may be provided for communication between server 109 and server 108a. Typically, the communication system between server 109 and 108a allows for bi-directional communication.

As described in detail further herein, pump status, alerts, alarms and other data is provided to clinicians via a personal digital assistant 118 having a display 118a and, if desired, an audible tone or sound generator (not shown). The digital assistant 118 communicates with the central system 108 via the central network 102, and in particular, wireless communication path or link 126 and cable communication system 110. As stated previously, one or more wireless access points 114 provide an interface, in a conventional manner, between the wireless communication paths and the cable communication system.

Preferably, communication between the central system 108 and the digital assistant 118 is bidirectional. Moreover, it is desired that the digital assistant 118 include enough memory and processing capability store and execute a module or application (not shown) for testing the integrity of the communication link between the digital assistant and the central system 108 or the wireless access point 114.

Preferably, but not necessarily, the module or application installed on the digital assistant 118 is a script or other computer instructions (i.e., software code) written in a high-level programming language, such as JAVA, that can be executed with or without clinician intervention. The module or application can test the integrity of the communication link by polling, or monitoring communication from, the central system 108, or the access point 114. If a response is not received from the central system 108 or the access point 114, module or application installed on the digital assistant 118 generates a time-out that results in audible tones and/or a notification on the visual display 118a that communication with the central system 108 has been lost. The notification on the visual display 118a can be, for example: the activation of an information pop-up window stating that the communication link is lost, or the changing of an active icon display on the toolbar of the display. As used herein, and recognized by those having ordinary skill in the art, a time-out is an output generated by a module or application for indicating that the module or application has waited a certain amount of time for input, but has not received it.

Preferably, the notification provided on the visual display 118a indicates to the clinician that data presented by the digital assistant 118 is not current, and access to alerts and alarms is not available. Conversely, the visual display 118a can indicate when the digital assistant 118 is linked to the central system 108 for providing realtime access to alerts and alarms.

As stated previously, clinicians within a healthcare facility have access to infusion alerts, alarms, and messages via a remote wireless device such as a personal digital assistant (PDA) 118 or other computer devices, wireless or hardwired to the network, such as a tablet computer with a bar code reader operably attached, or a laptop computer attached to an IV pole and having a bar code reader operably attached to the computer.

Preferably, the infusion system provides clinicians and other users with options for automating alert event-driven messages. Moreover, healthcare facility administrators and other users can customize the types of automated messaging to appear, via the remote wireless device, by message type or classification, severity of abnormality, and time based reminders. Additionally, the infusion system provides clinicians and other users with the ability to configure audible messages, visual messages, or both.

The messaging provided by the infusion system preferably includes a user configurable rules engine, a scheduler, and interfaces to infusion pump systems. Moreover, it is desired that the results-driven messaging provide clinicians with real-time decision support at the point of care via a workstation, electronic tablet, wireless personal digital assistant, or the like.

Turning back to FIG. 1, patient care system 100 preferably includes a computerized physician order-entry module (CPOE), an inpatient pharmacy module, a wireless nurse charting system, and an electronic patient medical record. It is desired that patient care system 100 provide a comprehensive patient safety solution for the delivery of medication. Within patient care system 100, software modules are provided to link together existing patient care systems using interfaces such as HL7 interfaces that are known to those having ordinary skill in the art. Preferably, the patient care system 100 operates on a variety of computers and personal digital-assistant products to transmit orders, update patient medical records, and access alerts, alarms, and messages.

The computerized physician order-entry module enables physicians to enter medication orders, access alerts, alarms, messages, reminders, vital signs and results. A pharmacy module checks the prescribed drug against documented patient allergies, and for compatibility with other drugs and food. The pharmacy module also provides real-time data for inventory management. A nurse medication-charting module provides clinical information that is immediately available at the bedside, thus ensuring verification of medication and dosage at the point-of-care.

Patient care system 100 integrates drug delivery products with the information required to assist in ensuring safe and effective delivery of medication. The clinical decision support and accompanying alerts, alarms, warnings, and messaging of the patient care system 100 provide a safety net of support for clinicians as they deliver patient care under increasing time and cost pressures. This information is preferably supplied through a wireless network that supplies data in a way that improves clinician workflow, making delivery of care easier.

The infusion system 210 (FIG. 2) within the patent care system 100 provides computerized prescribing and an electronic medical administration record (eMAR). Infusion system 210 puts charting, medication history, inventory tracking, and messaging at the clinician's fingertips. Patient care system 100 combines bar-coding and real-time technology to assist in ensuring that the right patient gets the right medication and the right dosage, at the right time, via the right route. Infusion system 210 provides alerts, alarms, messages, and reminders such as, but not limited to, lab value, out of range, and missed dose. As part of the verification of the right dosage, the system can also provide verification of the settings of an infusion pump.

As explained in detail further herein, the infusion system 210 resides, at least in part, on one or more electronic computing devices such as wireless remote personal digital assistants, workstations, physician order-entry modules, electronic tablets, processor controlled infusion pumps, or the like. The infusion system 210 can be configured to display, via one or more of the electronic computing devices, numerous hospital definable alerts and alarms in varying forms. In an embodiment, time-based alerts are provided to remind clinicians to perform a patient care function such as, but not necessarily limited to, changing an infusion rate. Further, emergency alarms are provided such as, but not necessarily limited to, an infusion being disconnected. Moreover, less urgent message are provided such as, but not necessarily limited to, the infusion being completed or the line being occluded. In addition, the infusion status can be viewed from anywhere within the healthcare facility via one or more of wireless remote personal digital assistants or other electronic computing devices.

In an embodiment, the system 210 provides for the escalation of alarms or alerts that are not indicated as corrected within a predetermined period of time. Conditions that can result in the escalation of an alarm or an alert are preferably defined by the health care facility. Likewise, the time before an alarm or alert escalates can also be defined by the health care facility. Accordingly, predefined alarms or alerts that are not corrected by a clinician within a predefined period of time with result in the escalation of the associated alarms or alerts. Thus, the frequency that the clinician is notified by the system of the escalated alarms or alerts is preferably increased, as can be the volume of the audible tones associated therewith.

As will be appreciated by those having skill in the art, the infusion system 210 assists in ensuring patient safety by checking the infusion being administered with the patient's order. As explained in detail further herein, a bar coding scheme is used wherein the infusion bag and patient are scanned, the infusion information is displayed on both an electronic computing device and the pump to assist in ensuring that the right infusion is being administered to the right patient and the right time and by the right route and at the right rate. In an embodiment, an alert, audible and visual appears on the electronic device if the above administration "rights" do not match. Moreover, when the clinician sets the infusion pump rate, an audible and visual alert appears on the electronic computing device if the programmed settings do not match the patient's infusion order. In addition, at any time the clinician can, via the electronic device, check the settings of an infusion pump to confirm if the settings match the infusion order as contained within the central database 108b.

In an embodiment, the infusion system 210 provides alerts and alarms, via one or more of the electronic computing devices or the like, with differing tones or phrases for fast identification of the severity or urgency of the message. Desirably, conventional infusion pump alerts and alarms can be displayed on the electronic computing devices, such as, but not necessarily limited to, a personal digital assistant, to keep the clinicians informed of the status of the infusions for all assigned patients, thereby saving time in resolving problems and improving workflow safety.

All alarms and alerts are preferably retrievable from a central system database for, inter alia, reporting purposes. The retrievable data can assist a healthcare facility in examining and analyzing how many medication errors were avoided through alarms, alerts, and warnings.

Desirably, the audible alerts and alarms are configured to sound differently according to the severity or urgency associated with the message or issue. Alarms requiring immediate attention sound different from less emergent alerts. Visual text describing the problem is preferably displayed by one or more of the electronic computing devices. In an embodiment, an alert sounds on a personal digital assistant when an infusion is nearing completion or is completed. The personal digital assistant also displays the patient, location, infusion type, and the time remaining before the infusion bag is empty. At all times the clinician can access, via the personal digital assistant, the status of infusions and thus react accordingly. In an embodiment, before visiting a patient room, the clinician can view the status of the infusions on the personal digital assistant to determine whether another bag will be needed in the near future. If another infusion bag is needed, the clinician can save time be taking the new bag on the first visit, rather than realizing a new bag is needed after arriving in the patient room. Similarly, the pharmacy can view the status, including time remaining, in order to schedule the mixing and delivery of the next infusion bag.

If desired, and as will be appreciated by those having skill in the art, other alarms and alerts related to the infusion pump can be made available on the electronic computing devices remotely located from the infusion pump. Pertinent information can be displayed on the electronic computing devices, thus saving the nurse time and steps in resolving the problem. As indicated above, when a pump alarms or alerts, the clinician can view patient information, drug order, and alarm or alert message on the personal digital assistant, and gather necessary items before going to the patient room to physically correct the alarm or alert condition.

In an embodiment, the infusion system 210 provides configurable time based alerts for reminding clinicians of scheduled infusion orders. As such, a tapering order to run NS at 200 ml/hr for two hours, then reduce to 50 ml/hr, results in the infusion system 210 alerting the nurse two hours after starting the infusion to reduce the rate. Further, late alerts are provided for informing clinicians when scheduled infusions are past the time tolerance set by the facility. Moreover, time based protocols such as alerts for conducting pains assessments such as after starting an epidural morphine infusion are generated.

Configurable aspects of the infusion system 210 also include the audible alerts emitted by the electronic computing devices, such as personal digital assistants. Preferably, the audible alerts can be configurable by the healthcare facility and within specific units of the healthcare facility to satisfy the unique environments within the healthcare facility.

As indicated previously, a plurality of visual alerts and messages can be displayed by the electronic computing devices, such as personal digital assistants, for indicating the importance or urgency of the message. Desirably, color, flashing, and bold text are display messaging options. Additionally, hyperlinks can be provided when messages are generated. Icons on the displays can also be utilized and emergency messages can be configured to interrupt the handheld electronic device, or the like, to immediately alert the clinician.

As also indicated previously, the infusion system 210 allows a clinician to view all infusions or assigned patients on the electronic computing device, such as a personal digital assistant or the like, thus reducing time spent traveling to and from patient rooms. Moreover, prescription information is displayed on the electronic computing device for verification of the drug amount, diluent, dose, and rate of the infusion. Additionally, real time status of the infusion is viewable for displaying milliliters per hour or the like, duration of the infusion, volume infused, time remaining, and volume yet to be infused. As indicated previously, the status of the infusion can be viewed, and flow rate history, from anywhere within the healthcare facility via the electronic computing devices.

As described in detail further herein, the infusion system 210 calculates ordered doses based on patient weight and displays the appropriate rate to run the infusion. Messages are generated if the infusion is set to run outside of the ordered dose. Moreover, pediatric dosing is available and configured for pediatric units within the healthcare facility.

In an embodiment, the status of primary infusions and secondary infusions, such as piggyback, are displayed by the infusion system 210 on the electronic computing device, such as a personal digital assistant. The clinician can check the volume left to infuse in a piggyback at any time and a message is displayed when the piggyback is completed and the primary infusion has resumed. In addition, messages are sent to the pharmacy to replenish stocks and infusion orders.

If desired, the infusion system 210 allows for the healthcare facility to define system infusion limits for warning a clinician who programs an infusion to run outside of the set range. The warning can be configured to allow clinicians to override the warning or prohibit overrides. As will be appreciated by those having ordinary skill in the art, prohibiting overrides for certain infusions may prevent a patient from inadvertently receiving an overdose.

The infusion system 210 can also provide for displaying reference information pertinent to the needs of each speciality unit within the healthcare facility. Drug information is viewable on the electronic device, such as a personal digital assistant, in addition to speciality unit policies and procedures. Protocols and standard orders can be configured to provide messages based on patient condition. In an embodiment, for example, heparin infusion protocols are configured to alert the clinician of a new blood glucose result and to titrate the insulin infusion by a determined number of milliliters based on the sliding scale protocol.

Moreover, through configured rules, messages are sent alerting the nurse of particular infusions as they relate to the patient's condition. In an embodiment, for example, a message is generated when a patient receiving a nephrotoxic infusion has an increase in BUN and Creatinine. Additionally, protocols can be configured to generate messages when certain infusions are titrated. In an embodiment, for example, a message to document a blood pressure can be configured when a clinician titrates a dopamine infusion. Furthermore, hemodynamic monitoring parameters can be linked to infusions to generate messages.

As indicated previously, new infusion orders can be configured to provide messages alerting the clinician of a new order. Messages can be configured as audible and visual such as textual, color alerts, flashing hyperlinks, icons, and the like. Stat orders and discontinue orders can be configured as a high priority message to differentiate them from non-urgent messages.

Preferably, educational messages are generated and configured by the healthcare facility. In an embodiment, for example, an infusion requiring a specific tubing set results in the display of a message informing the clinician. In a further embodiment, for example, an infusion requiring central venous access results in the display of a warning not to infuse in the peripheral vein.

In an embodiment, scheduling messages are generated and displayed on one or more electronic computing devices to remind users to complete the next task. Alerts to change infusion rates at scheduled times are sent to the electronic computing devices, such as in the case of a tapering infusion. Additionally, protocols with time-based alerts can be configured such as, for example blood infusion protocols.

Turning to FIG. 1, and as indicated above, patient care system 100 allows medication ordering, dispensing, and administration to take place at the patient's bedside. Physicians can order simple and complex prescriptions, intravenous therapy and total parental nutrition therapy (TPN) using a wireless handheld device. Infusion system 210 checks for drug interactions and other possible errors as well as correct dosage. Infusion system 210 then transmits this data in real-time to the patient care facility or local pharmacy, hospital nursing unit, home care unit, and/or clinic.

The clinician can access a medical records database using a handheld scanning device. In an embodiment, the clinician scans the bar coded medication and the patient's bar coded bracelet to confirm the presence of the right medication, dosage, and time before administering any drugs. Infusion system 210 updates medical and administrative records, thereby eliminating most, if not all, time-consuming paperwork. Thus, infusion system 210 can reduce costs and improves efficiency while possibly saving lives. Patient care system 100 can include access-controlled mobile and stationary medication and supply depots, including electronic patient medical records and computerized prescribing, providing complete preparation and inventory management from the point of care to the pharmacy.

As mentioned previously, FIG. 1 is a graphical representation of patient care system 100. The patient care system 100 includes a pharmacy computer 104, a central system 108, and a treatment location 106, linked by a network 102. In an embodiment, the pharmacy computer 104 includes a processing unit 104a, a keyboard 104b, a video display 104c, a printer 104d, a bar code reader 104e, and a mouse 104f. Although not shown in FIG. 1, the patient care system 100 can also include subsystems for hospital administration, nursing stations, a clinical information subsystem, a hospital information subsystem, an Admissions Discharge and Transfer (ADT) subsystem, a billing subsystem, and/or other subsystems typically included in conventional patient care systems.

In an embodiment, the central system 108 includes a central servicing unit 108a, a database 108b, a video display 108c, input/output components, and other conventional hardware components known to those having ordinary skill in the art. The network 102 preferably includes a cable communication system 110 portion and a wireless communication system portion. The cable communication system 110 can be, but is not limited to, an Ethernet cabling system, and a thin net system.

In an embodiment, the treatment location 106 can include a treatment bed 106a, an infusion pump 120, and medical treatment cart 132. In FIG. 1, a clinician 116 and a patient 112 are shown in the treatment location 106. Medication 124 can be of a type that is administered using an infusion pump 120. Medication 124 can also be of a type that is administered without using an infusion pump. The medication can be stored in medication storage areas 132a of medical treatment cart 132. The clinician 116 uses a digital assistant 118 in the process of administering medication 124 to the patient 112.

In an embodiment, the clinician 116 uses the digital assistant 118 in the course of treating patient 112 to communicate with the cable communication system 110 of the network 102 via a first wireless communication path 126. The infusion pump 120 has the ability to communicate with the cable communication system 110 via a second wireless communication path 128. The medication cart 124 also has the ability to communicate via a wireless communication path (not shown in FIG. 1). A wireless transceiver 114 interfaces with the cable communication system 110. The wireless communication system portion of the network can employ technology such as, but not limited to, known to those having ordinary skill in the art such as IEEE 802.11b "Wireless Ethernet," a local area network, wireless local area networks, a network having a tree topography, a network having a ring topography, wireless internet point of presence systems, an Ethernet, the Internet, radio communications, infrared, fiber optic, and telephone. Though shown in FIG. 1 as a wireless communication system, the communication paths can alternatively be hardwired communication paths.

In the patient care system 100, a physician can order medication 124 for patient 112. In an embodiment, the order can originate with a clinician 116 at the treatment location 106. The physician and/or clinician 116 can use a computerized physician order entry system (CPOE), the medical cart 132, or a like device, to order the medication 124 for the patient 112. Those having ordinary skill in the art are familiar with conventional computerized physician order entry systems. Despite its name, any clinician 116 can use the computerized physician order entry system. If the medication 124 is efficient to administer through infusion pump 120, the infusion order includes information for generating operating parameters for the infusion pump 120. The operating parameters are the information and/or instruction set necessary to program infusion pump 120 to operate in accordance with the infusion order.

The infusion order can be entered in a variety of locations including the pharmacy, the nursing center, the nursing floor, and treatment location 106. When the order is entered in the pharmacy, it can be entered in the pharmacy computer 104 via input/output devices such as the keyboard 104b, the mouse 104f, a touch screen display, the CPOE system and/or the medical treatment cart 132. The processing unit 104a is able to transform a manually-entered order into computer readable data. Devices such as the CPOE can transform an order into computer readable data prior to introduction to the processing unit 104a. The operating parameters are then printed in a bar code format by the printer 104d on a medication label 124a. The medication label 124a is then affixed to a medication 124 container. Next, the medication 124 container is transported to the treatment location 106. The medication 124 can then be administered to the patient 112 in a variety of ways known in the art including orally and through an infusion pump 120. If the medication 124 is administered orally, the clinician 116 can communicate via the digital assistant 118 and/or the medical cart 132. The medical cart 132 is computerized and generally has a keyboard (not shown), a display 132b, and other input/output devices such as a bar code scanner (not shown).

As will be appreciated by those having ordinary skill in the art, the infusion bag can also be premixed, wherein a non-patient specific bar code is attached to the bag identifying the medication 124. Moreover, the infusion bag can be mixed in the pharmacy or on the floor, wherein a patient specific bar code is attached to the bag that identifies the medication 124 and, if desired, when the medication is to be administered to the patient.

At the treatment location, the medication 124 can be mounted on the infusion pump 120 with an intravenous (IV) line 130 running from the infusion pump 120 to the patient 112. The infusion pump 120 can include a pumping unit 120a, a keypad 120b, a display 120c, an infusion pump ID 120d, and an antenna 120e. Prior art infusion pumps can be provided with a wireless adaptor (not shown) in order to fully implement the system 100. The wireless adaptor can have its own battery if necessary to avoid reducing the battery life of prior art infusion pumps. The wireless adaptor can also use intelligent data management such as, but not limited to, store-and-forward data management and data compression to minimize power consumption and network traffic. The wireless adaptor can also include the ability to communicate with the digital assistant 118 even when the network 102 is not functioning.

In an embodiment, the patient care system 100 can include a variety of identifiers such as, but not limited to, personnel, equipment, and medication identifiers. In FIG. 1, the clinician 116 can have a clinician badge 116a identifier, the patient 112 can have a wristband 112a identifier, the infusion pump 120 can have an infusion pump ID 120d identifier, and the medication 124 can have a medication label 124a identifier. Clinician badge 116a, wristband 112a, infusion pump ID 120d, and medication label 124a include information to identify the personnel, equipment, or medication they are associated with. The identifiers can also have additional information. For example, the medication label 124a can include information regarding the intended recipient of the medication 124, operating parameters for infusion pump 120, and information regarding the lot number and expiration of medication 124. The information included in the identifiers can be printed, but is preferably in a device readable format such as, but not limited to, an optical readable device format such as a bar code, a radio frequency (RF) device readable format such as an RFID, an iButton, a smart card, and a laser readable format. The digital assistant 118 can include a display 118a and have the ability to read the identifiers including biometric information such as a fingerprint.

The wristband 112a is typically placed on the patient 112 as the patient 112 enters a medical care facility. The wristband 112a includes a patient identifier. The patient identifier can include printed information to identify the patient and additional information such as a treating physician's name(s). The patient identifier for patient 112 can include information such as, but not limited to, the patient's name, age, social security number, the patient's blood type, address, allergies, a hospital ID number, and the name of a patient's relative. In an embodiment, the patient identifier can contain a unique reference code or password for the patient, which is also stored in the central database for cross referencing, if needed or desired.

FIG. 2 is a block diagram of a computer 200 representative of the pharmacy computer 104, the central system 108, the CPOE, the digital assistant 118 of FIG. 1, and/or a computer included in any number of other subsystems that communicate via the network 102 such as the medication treatment cart 132. As indicated previously, the computer 200 includes an infusion system 210, or a portion of infusion system 210, for use within the patent care system 100. The infusion system as described in reference to FIG. 2 is preferably a computer program. However, the infusion system can be practiced in whole or in part as a method and system other than as a computer program.

A critical concern in the art is that the right medication is administered to the right patient. Therefore, infusion system 210 includes features to assist in assuring that the right medication is administered to the right patient in an efficient manner. Infusion system 210 can be implemented in software, firmware, hardware, or a combination thereof. In one mode, infusion system 210 is implemented in software, as an executable program, and is executed by one or more special or general purpose digital computer(s), such as a personal computer (PC; IBM-compatible, Apple-compatible, or otherwise), personal digital assistant, workstation, minicomputer, or mainframe computer. An example of a general-purpose computer that can implement the infusion system 210 of the present invention is shown in FIG. 2. The infusion system 210 can reside in, or have various portions residing in, any computer such as, but not limited to, pharmacy computer 104, central system 108, medication treatment cart 132, and digital assistant 118. Therefore, the computer 200 of FIG. 2 is representative of any computer in which the infusion system 210 resides or partially resides.

Generally, in terms of hardware architecture, as shown in FIG. 2, the computer 200 includes a processor 202, memory 204, and one or more input and/or output (I/O) devices 206 (or peripherals) that are communicatively coupled via a local interface 208. The local interface 208 can be, for example, but not limited to, one or more buses or other wired or wireless connections, as is known in the art. The local interface 208 can have additional elements, which are omitted for simplicity, such as controllers, buffers (caches), drivers, repeaters, and receivers, to enable communications. Further, the local interface can include address, control, and/or data connections to enable appropriate communications among the other computer components.

Processor 202 is a hardware device for executing software, particularly software stored in memory 204. Processor 202 can be any custom made or commercially available processor, a central processing unit (CPU), an auxiliary processor among several processors associated with the computer 200, a semiconductor-based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc., or a 68xxx series microprocessor from Motorola Corporation. Processor 202 can also represent a distributed processing architecture such as, but not limited to, SQL, Smalltalk, APL, KLisp, Snobol, Developer 200, MUMPS/Magic.

Memory 204 can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, memory 204 can incorporate electronic, magnetic, optical, and/or other types of storage media. Memory 204 can have a distributed architecture where various components are situated remote from one another, but are still accessed by processor 202.

The software in memory 204 can include one or more separate programs. The separate programs comprise ordered listings of executable instructions for implementing logical functions. In FIG. 2, the software in memory 204 includes the infusion system 210 in accordance with the present invention and a suitable operating system (O/S) 212. A non-exhaustive list of examples of suitable commercially available operating systems 212 is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time Vxworks operating system from WindRiver Systems, Inc.; or (g) an appliance-based operating system, such as that implemented in handheld computers or personal digital assistants (PDAs) (e.g., PalmOS available from Palm Computing, Inc., and Windows CE available from Microsoft Corporation). Operating system 212 essentially controls the execution of other computer programs, such as infusion system 210, and provides scheduling, input-output control, file and data management, memory management, and communication control and related services.

Infusion system 210 can be a source program, executable program (object code), script, or any other entity comprising a set of instructions to be performed. When a source program, the program is translated via a compiler, assembler, interpreter, or the like, that may or may not be included within the memory 204, so as to operate properly in connection with the O/S 212. Furthermore, the infusion system 210 can be written as (a) an object oriented programming language, which has classes of data and methods, or (b) a procedural programming language, which has routines, subroutines, and/or functions, for example, but not limited to, C, C++, Pascal, Basic, Fortran, Cobol, Perl, Java, and Ada. In one embodiment, the system program 210 is written in C++. In other embodiments, the infusion system 210 is created using Power Builder. The I/O devices 206 can include input devices, for example, but not limited to, a keyboard, mouse, scanner, microphone, touch screens, interfaces for various medical devices, bar code readers, stylus, laser readers, radio-frequency device readers, etc. Furthermore, the I/O devices 206 can also include output devices, for example, but not limited to, a printer, bar code printers, displays, etc. The I/O devices 206 can further include devices that communicate as both inputs and outputs, for instance, but not limited to, a modulator/demodulator (modem; for accessing another device, system, or network), a radio frequency (RF) or other transceiver, a telephonic interface, a bridge, a router, etc.

If the computer 200 is a PC, workstation, personal digital assistant, or the like, the software in the memory 204 can further include a basic input output system (BIOS) (not shown in FIG. 2). The BIOS is a set of essential software routines that initialize and test hardware at startup, start the O/S 212, and support the transfer of data among the hardware devices. The BIOS is stored in ROM so that the BIOS can be executed when the computer 200 is activated.

When the computer 200 is in operation, processor 202 is configured to execute software stored within memory 204, to communicate data to and from memory 204, and to generally control operations of the computer 200 pursuant to the software. The infusion system 210 and the O/S 212, in whole or in part, but typically the latter, are read by processor 202, perhaps buffered within the processor 202, and then executed.

When the infusion system 210 is implemented in software, as is shown in FIG. 2, the infusion system 210 program can be stored on any computer readable medium for use by or in connection with any computer related system or method. As used herein, a computer readable medium is an electronic, magnetic, optical, or other physical device or means that can contain or store a computer program for use by or in connection with a computer related system or method. The infusion system 210 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

In another embodiment, where the infusion system 210 is implemented in hardware, the infusion system 210 can be implemented with any, or a combination of, the following technologies, that are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Any process descriptions or blocks in figures, such as FIGS. 3-11, are to be understood as representing modules, segments, or portions of hardware, software, or the like, that can include one or more executable instructions for implementing specific logical functions or steps in the process, and alternate implementations are included within the scope of the embodiments of the present invention in which functions can be executed out of order from that shown or discussed, including substantially concurrently or in reverse order, depending on the functionality involved, as would be understood by those having ordinary skill in the art.

Figure 4:
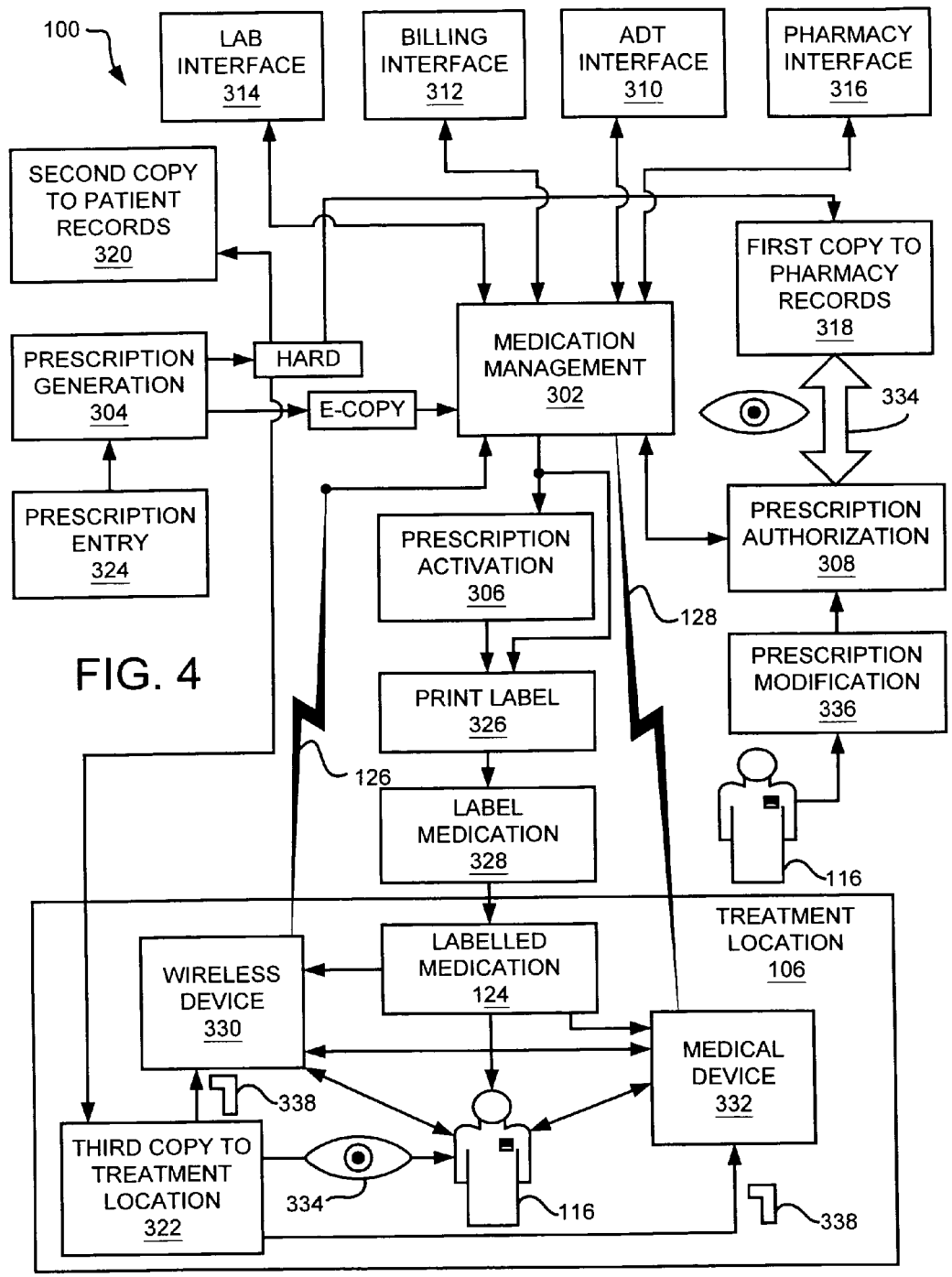
FIG. 4 is a block diagram showing functional components of the patient care system of FIG. 1.

FIG. 4 is a first block diagram showing functional components of the patient care system 100 of FIG. 1. As shown in FIG. 4, the patient care system 100 can be practiced as a modular system where the modules represent various functions of the patient care system, including the infusion system 210 (FIG. 2). The flexibility of the patient care system 100 and the infusion system can be enhanced when the systems are practiced as modular systems. The modules of the infusion system 210 (FIG. 2) can be included in various portions of the patient care system 100. In an embodiment, the patient care system functional components can include, inter alia, a medication management module 302, a prescription generation module 304, a prescription activation module 306, and a prescription authorization module 308.

The medication management module 302 can coordinate the functions of the other modules in the patient care system 100 that are involved in the administration of medical treatment. The medication management module 302 generally coordinates with other portions of the patient care system 100. The medication module 302 can include sub-modules for operating and/or interfacing with a CPOE, for operating and/or communicating with point-of-care modules, and for operating and/or communicating with medical treatment comparison modules. In FIG. 4, an admissions, discharge, and transfer (ADT) interface 310, a billing interface 312, a lab interface 314, and a pharmacy interface 316 are shown. The ADT interface 310 is used to capture information such as the patient's demographics, size, weight, and allergies. Pharmacy interface 316 imports orders from the pharmacy. The pharmacy interface 316 can be an HL7 type of interface that interfaces with other systems for entering orders, such as a CPOE. This ability reduces the necessity for entering data into the patient care system 100 more than once. The pharmacy interface 316 can be configured to communicate with commercially available systems such as, but not limited to Cerner, HBOC, Meditech, SMS, Phamous, and the like. Various other interfaces are also known to those having ordinary skill in the art but are not shown in FIG. 4.

The medication management module 302 can have additional features such as the ability to check for adverse reactions due to drug-to-drug incompatibility, duplicate drug administration, drug allergies, drug dosage limitations, drug frequency limitations, drug duration limitations, and drug disease contraindications. Food and alcohol interactions can also be noted. Drug limitations can include limitations such as, but not limited to, limitations associated with adults, children, infants, newborns, premature births, geriatric adults, age groupings, weight groupings, height groupings, and body surface area. In an embodiment, the medication management module 302 prevents the entry of the same prescription for the same patient from two different sources within the patient care system 100.

The medication management module 302 can also include the ability to generate reports. The reports include, but are not limited to, end-of-shift, titration information, patient event lists, infusion history, pump performance history, pump location history, and pump maintenance history. The end-of shift report can include the pump channel, start time, end time, primary infusion, piggyback infusion, medication, dose, rate, pump status, volume infused, volume remaining, time remaining, and the last time cleared. The infusion history report includes medications and volume infused.

The medication management module 302 can also include a medical equipment status database. The medical equipment status database includes data indicating the location of a medical device 332 within the patient care system 100. The medical equipment status database can also include data indicating the past performance of a medical device 332. The medical equipment status database can also include data indicating the maintenance schedule and/or history of a medical device 332.

Infusion prescriptions are entered in prescription entry 324. Prescriptions can include prescriptions such as, but not limited to, single dose infusions, intermittent infusions, continuous infusions, sequencing, titrating, and alternating types. Infusion prescriptions can also include total parenteral nutritional admixtures (TPN), chemotherapy continuous infusion, piggybacks, large volume parenterals, and other infusion prescriptions. The patient care system 100 can function without end dates for orders. The patient care system 100 uses a continuous schedule generator that looks ahead a predefined time period and generates a schedule for admixture filling for the time period. The predefined time period can be defined at the patient care system 100 level or at subsystem levels such as the clinical discipline level and an organizational level. The predefined time periods can be adjustable by the clinician 116 entering the order. The schedule can be automatically extendable as long as the order is active in the patient care system 100.

The prescription generation module 304 generates hard prescriptions and electronic (E-copy) prescriptions. Hard prescriptions are generally produced in triplicate in medical facilities. A first hard copy 318 is generally sent to the is pharmacy, a second hard copy 320 is generally kept for the patient's records, and third hard copy 322 is sent to treatment location 106. An electronic prescription is sent to the medication management module 302.

Prescription generation module 304 can include confirming operating parameters. The operating parameters can be based on information from prescription entry module 324. Prescription generation 304 can occur anywhere in the patient care system 100 such as, but not limited to, the pharmacy, the treatment location 106, and a nursing center.

A computerized physician order entry (CPOE) system or the like can be employed to carry out some or all of the functions of the prescription generation module 304. Clinicians 116 can enter data in a variety of manners such as, but not limited to, using a tablet wireless computer, personal digital assistant, treatment cart 132, and a workstation. The medication management module 302 can interface with more than one prescription generation module 304. The medication management module can receive orders from anywhere within the patient care system 100.

The pharmacy computer 104 is able to access the electronic copy from the medication management module 302. The prescription activation module 306 is a computer assisted system for coordinating the filling and labeling of prescriptions. The filling of the prescription and the creation or location of medication 124 from stock is handled by the prescription activation module 306. In an embodiment, the filling process results in the creation of the medication label 124, as opposed to the prescription activation process.

The patient care system 100 can bypass the prescription activation module 306. This can occur if the ordering clinician 116, such as the patient's physician, has the authority to immediately activate an order. If the order is immediately activated, the medication management module 302 can go directly to filling and thus, the prescription labeling module 326.

In block 326, the patient care system 100 prints the medication label 124. The prescription can be printed remotely and will often be printed by the pharmacy printer 104d. After block 326, the patient care system goes to block 328. In block 328, the medication label 124a is attached to the medication 124. The pharmacist generally provides a visual verification 334 that the medication label 124a matches the first hard copy 318 of the prescription. FIG. 4 shows that a visual verification 334 is also associated with prescription authorization module 308. The medication 124 can then be transported from the pharmacy to the treatment location 106. A portable medical treatment cart 132 can be used for a portion of the route from the pharmacy to the treatment location 106.

The medication label 124a can include information for preparing the infusion bag. If not generated within patient care system 100, medication label 124a can be provided by a bulk medication supplier. If provided by a bulk medication supplier, the patient care system 100 gathers the information from the medication label 124a. In addition, the patient care system 100 can add information, such as a patient identifier, to the medication label 124a.

The medication labeling module 328 places the medication label 124 on the medication 124. This can be accomplished manually. This can also be accomplished using an automatic prescription filling and packaging system (not shown). If an automatic filling and packaging system is used, medication labeling module 328 provides data for coordination of the labeling of the medication 124 to the filling and packaging system.

At the treatment location 106, the clinician 116 uses a wireless device 330, such as digital assistant 118 and/or medical treatment cart 132, to verify and administer medication 124 to the patient 112. Wireless device 330 communicates with the medication management module 302 via a communication path, such as first communication path 126.

Clinician 116 can identify his/herself by scanning badge 116a, identifies the patient 112 by scanning wristband 112a, identifies the medication 124 by scanning medication label 124a, and identifies the medical device 332, such as infusion pump 120, by scanning label 120d. Clinician 116 can also identify his/herself by providing a fingerprint and/or password. The medical device 332 can be a medical device capable of two-way communication with the medication management module 302. Alternatively, the medical device 332 can only be capable of providing information to the medication management module 302. The infusion program 210 assists the clinician 116 in administering and verifying the medical treatment. The infusion program 210 can include downloading of operating parameters to the medical device 332. Clinician 116 can provide a visual verification to confirm the third copy 322 and/or the MAR matches the labeled medication 124. Scanner 338 can be used to enter machine readable information from the third copy 322 to the wireless device 330 and the medical device 332.

The patient care system 100 can make adjustments and modifications to infusion orders. Among other modules that can include the ability to make infusion adjustments are prescription entry 324, prescription activation 306, prescription authorization 308, and prescription modification module 336. Clinician 116 accesses the prescription modification module 336 in order to make adjustments to an order. The clinician 116 can access the prescription modification module 336 throughout the patient care system 100. However, one very useful location for clinician 116 to access the prescription modification module 336 is at treatment location 106.

In prescription authorization module 308, the patient care system 100 determines whether the clinician 116 has the authority to independently modify an infusion order. The clinician 116 can be recognized by the patient care system 100 as having the authority to independently modify certain portions of the order. If the clinician 116 does not have the authority to independently modify the order, a pharmacist or physician can be requested to approve the modification entered by the clinician 116.

In one implementation of patient care system 100, an order is entered in pharmacy computer 104. The order includes a first patient identifier and an operating parameter. The pharmacy computer 104 generates a medication label 124a that is affixed to the medication bag or container. The medication 124 is sent to a treatment location 106. At treatment location 106, clinician 116 reads the clinician's badge 116a, patient's wristband 112a, and medication label 124a with a digital assistant 118. The digital assistant 118 reports, based on a determination made by the central system 108, whether medication label 124a and wristband 112a correspond to the same patient 112. The system 400 then sends the medication identifier to the pharmacy computer 104. The pharmacy computer 104 confirms the medication label 124a identifies the same patient as the order and sends the operating parameter to an infusion pump. The operating parameter can be sent directly to the infusion pump 120. The operating parameter is then used to program the infusion pump to administer the medication 124 to the patient 112.

Figure 5:
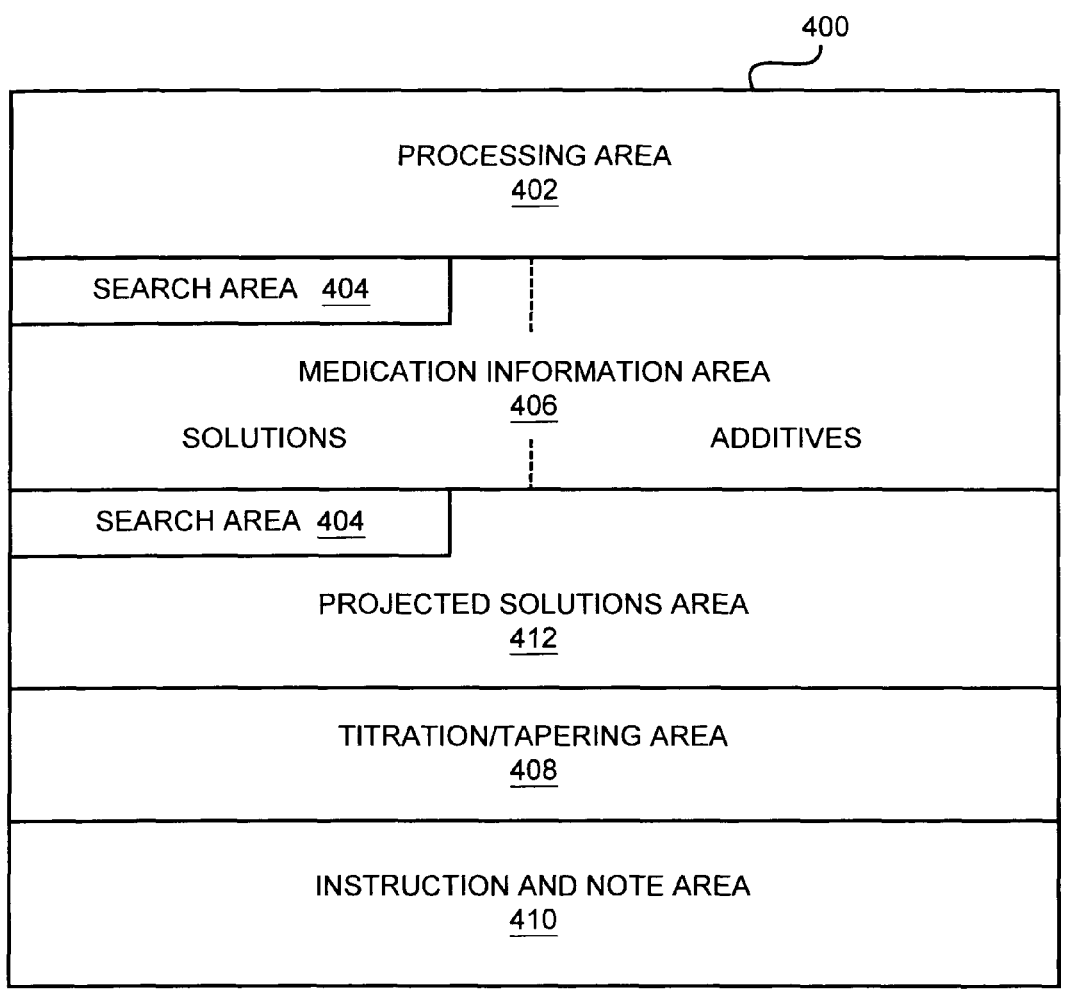
FIG. 5 is an exemplar computer screen for implementing various functions of the patient care system of FIG. 1.

FIG. 5 is an exemplar block diagram of a computer screen 400 that is useful in implementing various functions of the infusion system 210 (FIG. 2). In addition to other functions, the computer screen 400 can be used to enter new infusion orders, to modify existing infusion orders, and to stop infusion orders. Computer screen 400 preferably includes a processing area 402, search areas 404, a medication information area 406, a titration/Tapering criteria area 408, an instruction and note area 410, and a projected solution ingredient area 412. Infusion medication order types include single dose, intermittent, continuous, sequencing, and alternating. Computer screen 400 can be used with digital assistant 118, pharmacy computer 104, infusion pump 120, a CPOE system, and medical treatment cart 132. Computer screen 400 is generally designed to have the look-and-feel of clinician accessible computer screens throughout the patient care system 100 of FIG. 1. The functions of computer screen 400 are partially accomplished with database linkage techniques familiar to those having ordinary skill in the art such as, but not limited to, hyperlinks, definition boxes, and dropdown menus.

The processing area 402 includes the ability to trigger the creation of an infusion order, a save of an infusion order, the modification of an infusion order, and a cancellation of an infusion order. Clinician 116 can customize the computer screen 400 to provide the clinician's 116 preferred order entry procedures. The processing area 402 includes a status indicator for orders. The processing area 402 also includes an area for indicating whether a PRN order ("as required" or "when needed" order) can be placed by clinician 116. The processing area 402 further includes the ability to display and adjust medical device 332 operating parameters, infusion order route, infusion line, infusion administration site, infusion order start time, infusion medication order type, infusion flow rate tolerance, infusion flow rate, infusion duration, area of preparation (such as pharmacy or a remote site). The processing area 402 can also include an area for linking medical orders to other medical orders such as, linking a physician's infusion order to another medical order entered by another clinician 116. The processing area 402 can include a trigger for displaying data in other areas of the computer screen 400 such as, but not limited to the projected solutions area 412.

Search areas 404 allow for searching for medications, solutions and/or additives for infusion orders. Default diluents can be provided for orders. If a default dosage for a medication is defined in the patient care system 100, the default dosage automatically appears with the search result that includes the medication. A search from search area 404, can result in the display of the medication name, the route of administration, the cost, the package size, the dosage form, the generic name, whether the medication is a narcotic, whether the medication is controlled, whether formulary, and whether the medication is manufactured.

Medication information area 406 can be used to define infusion order additives and solutions. Medication information area 406 can include separate additive areas and solution areas. The solution area can include a label "Solution/Diluent". The patient care system 100 may use a medication 124 database, a solutions database, and an additive database to populate the medication information area 406 with medications 124, solutions, and additives. Substances identified in one database may also be identified in other databases. The databases may be linked to provide default values for combinations of the medications 124 and solutions.

Titration/tapering criteria area 408 generally applies to continuous infusion orders. Titration defines certain parameters of an order such as dosage and/or flow rate. Dose and flow rate can be entered as an absolute. Also, mathematical symbols such as, but not limited to, greater than ">", less than "<", and equal "=", can be used alone or in combination to enter information in titration/tapering criteria area 408. A calendar can also be used to enter data in titration/tapering criteria area 408. Dosage and flow rate can also be entered as an acceptable range. Titration/tapering criteria area 408 can be hidden when non-continuous infusion orders are entered and/or modified. The titration criteria can include values of various parameters related to patient condition such as, but not limited to, various lab results, vital signs, ability to take fluids orally, fluid input and output, and the like.

Instruction and note area 410 includes the ability to save information such as physician notes regarding a patient 112 and/or an infusion order. The instruction and note area 410 can include a display and lookup area for identifying clinicians 116 that are responsible for the patient 112, such as the patient's physician.

The projected solutions area 412 displays solution schedules and related ingredients based on the current state of the order being processed for patient 112. The time period projected can be a patient care system 100 default. The time period can also be adjustable by the clinician 116. The projected solutions area 412 can include an adjustable display indicating the time period projected by the patient care system 100. The data displayed in the projected solutions area is generally saved when an order save is triggered in the processing area 402. The projected solutions area 412 can include the ability to look back over a period of time while modifying a previously entered order. This allows the clinician 116 to view solutions that may have already been prepared according to the unmodified infusion order.

Figure 6:
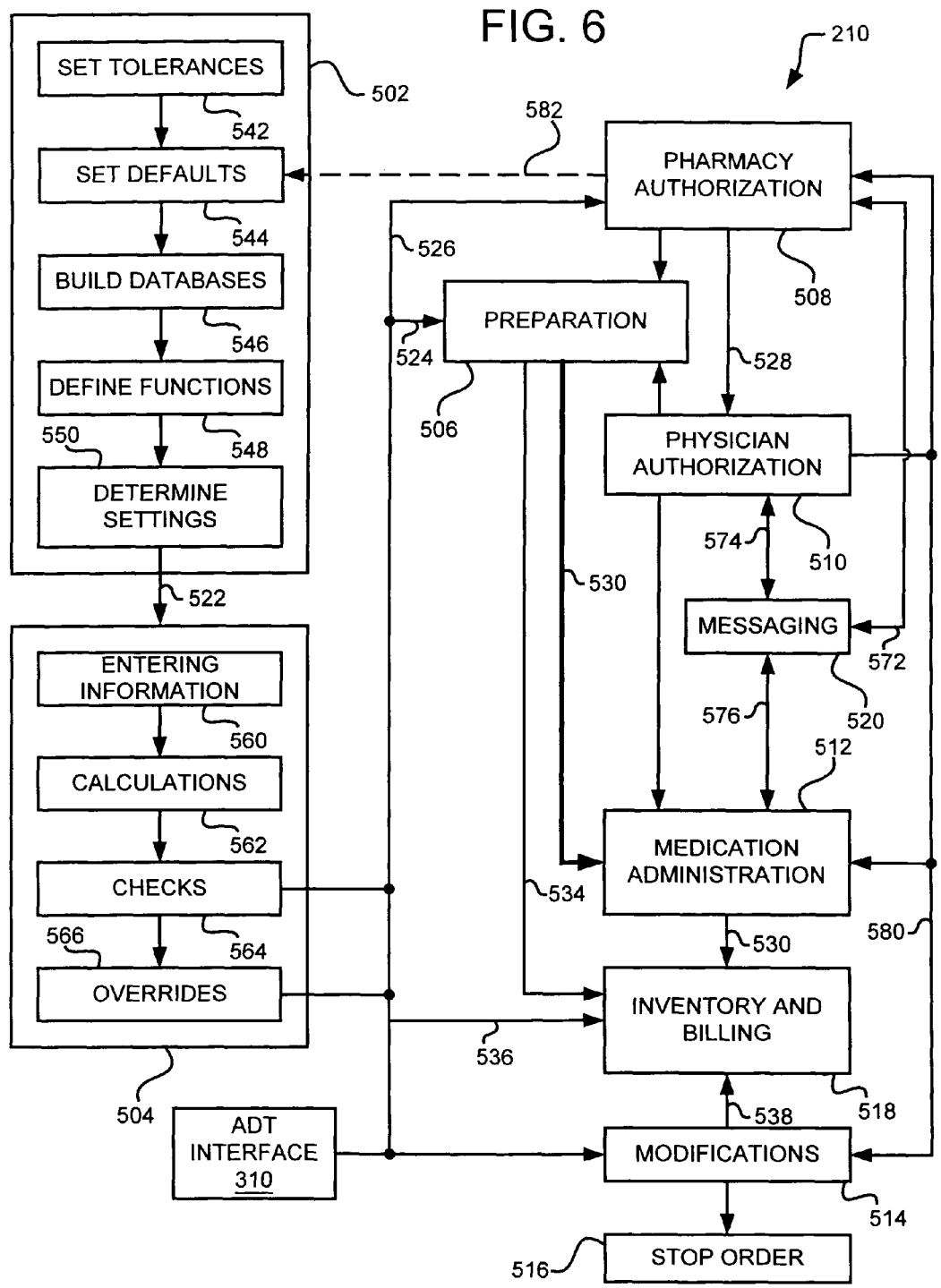
FIG. 6 is a block diagram showing functional components of the infusion system of FIG. 2. The functional components include, inter alia, blocks for setting infusion system parameters, infusion order creation, infusion order preparation, medication administration, infusion order modifications, and messaging.

FIG. 6 is a block diagram showing functional components of the infusion system 210 of FIG. 2. The functional components include blocks for setting system parameters 502, infusion order creation 504, infusion order preparation 506, medication administration 512, infusion order modifications 514, and messaging 520. FIG. 6 also includes blocks for pharmacy authorization 508, physician authorization 510, stop orders 516, and inventory and billing 518. FIG. 6 presents one description of the infusion system. However, FIG. 6 does not define a required series of steps for implementing the infusion system. One of the benefits of the infusion system is that a clinician 116 can access and enter information from a large number of locations, both physical and functional, within the patient care system 100. For example, an infusion order can be created by a physician using a CPOE, by a pharmacist using pharmacy computer 106, by a clinician 116 using digital assistant 118, and by a clinician using medication treatment cart 132. Moreover, vitals, lab results, and other records of patients can be checked from a large number of locations within the health care facility including, for instance, the inpatient pharmacy. Accordingly, a user within the inpatient pharmacy 104 (FIG. 1) can view, from a computing device 104c, the wards within the health care facility. Upon selection of a ward by the user, a patient list is provided wherein the user can select a patient and associated records for display on the computing device. Alternatively, the user can enter all or part of the patient's name into the computing device, whereby the records associated with the patient are provided by the computing device for selection by the user. Upon selection, the record(s) is displayed.

In an embodiment, FIG. 6 can be viewed as first preparing the patient care system 100 for receiving infusion orders—setting system parameters 502; second, creating the infusion order—infusion order creation 504; third, preparing the infusion order—preparation 506; fourth, authorizing the infusion order—pharmacy and physician authorization 508 and 510; fifth, administering the infusion order—medication administration 512; sixth, accounting for and replenishing the inventory used to prepare the infusion order and billing the patient for the infusion order—inventory and billing 518; seventh, modifying the infusion order—modifications 514; and eight, providing messages to various personnel and sub-systems regarding the progress of the infusion order, infusion, messages for assisting in ensuring that the right medication is efficiently prepared and provided to the right patient, in the right dose and at the right time, or the like—messages 520. Modifications 514 can include stopping the order—stop order 516—based on information provided by the transfer interface 310.

Setting system parameters 502 includes functional blocks that prepare the infusion system 210 to create and process infusion orders. Setting system parameters 502 include, but is not limited to, setting tolerances 542, setting defaults 544, building databases 546, defining functions 548, and determining system settings 550. Setting system parameters 502 is further described below in reference to FIG. 7.

Figure 8:
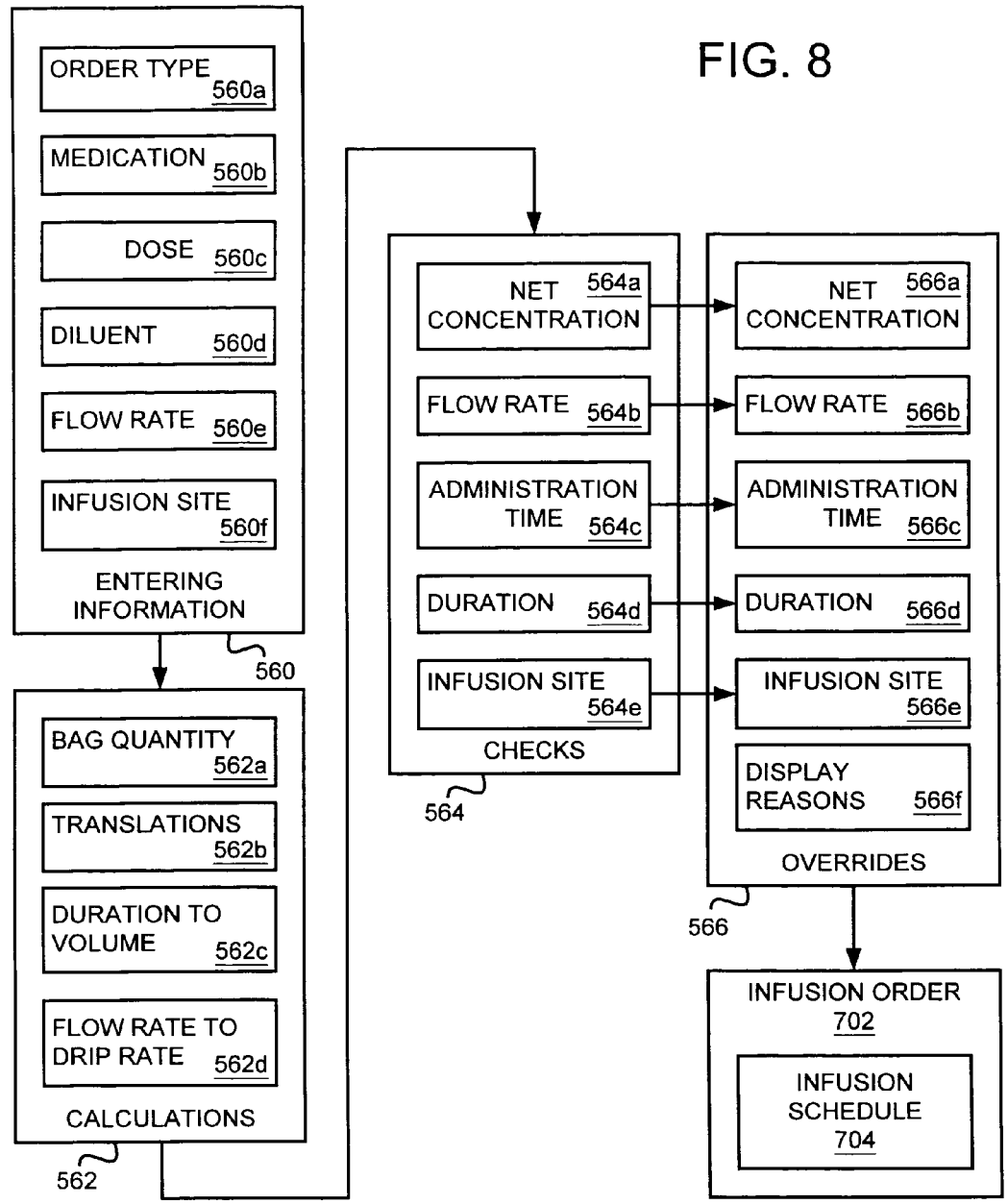
FIG. 8 is a block diagram showing functional components for the infusion order creation of FIG. 6.

Infusion order creation 504 includes functional blocks used to create infusion orders. Infusion order creation 504 includes functions similar to those described in reference to prescription generation 304 (FIG. 4). Infusion order creation 504 includes, but is not limited to, entering information 560, calculations 562, checks 564, and overrides 568. Infusion order creation is further described below in reference to FIG. 8. The result of infusion order creation is an infusion order 702 (FIG. 8). Infusion order 702 generally includes an infusion schedule 704 (FIG. 8).

Infusion orders can require authorization as described in reference to block 308 (FIG. 4). In FIG. 6, prescription authorization by the pharmacist and prescription authorization by the physician are considered separately in functional blocks for pharmacy authorization 508 and physician authorization 510. Physician authorization 510 may not be required if the infusion order is initiated by the physician. The infusion order generally requires pharmacy authorization 508 and physician authorization 510 if the order is generated by a clinician at the treatment location 106, other than the pharmacist or physician. However, if medication 124 is required immediately, the infusion system 210 allows administering clinicians to bypass prescription authorization 508 and physician authorization 510. In the case of emergency orders or non-emergency orders for routine medications, the infusion system 210 can determine there is no information stored in the patient care system 100 related to the medical treatment the clinician 116 desires to administer to the patient 112. If the infusion system 100 recognizes the clinician 116 as having the authority to initiate the desired medical treatment, the system 210 allows for the administration of the medical treatment without going to blocks 508 and 510. This authorization is then obtained following administration.

Infusion order preparation 506 can be accomplished in a number of locations throughout the medical facility such as, but not limited to, the pharmacy, the nursing center, on the floor, and the treatment location 106. Preparation 506 includes providing instructions for preparing the medication 124 and minimizing the possibility of errors in medication preparation.

Medication administration 512 takes place at the treatment location 106. The infusion system 210 is designed to make the administration of the order as efficient and accurate as possible. The infusion system 210 provides the administrating clinician with the tools to administer the right medication to the right patient in the right dose, with the right pump settings, at the right time, and via the right route. Should an alert, alarm, reminder, or other message be appropriate in assisting the clinician with the administration of the medication, the medication administration module provides a status information output to the messaging module 520. In response to the status information output, the messaging module 520 forwards a related text message, audible indicator enable, or both, to one or more electronic computing devices.

As known by those having skill in the art, infusion orders are frequently modified. Infusion system 210 provides modifications 514 to account for infusion order modifications. Modification 514 includes modifications to infusion duration, flow rate, infusion site, and stop orders 516. Modification 514 also includes the functional blocks required to implement infusion order modifications.

The infusion system 210 can include patient care system 100 wide defined stop orders 516. Changes in patient status may generate messages 520 for appropriate action. The infusion system 210 coordinates with the transfer interface 310 to automatically stop orders 516 upon discharge or death.

The system 100 includes inventory and billing module 518. Inventory and billing 518 allows the financial transactions associated with patient care to proceed with a minimum of human intervention. The completion of medication administration 512 can trigger patient billing through the billing interface 312. The billing interface can include an HL7 interface. If patients are to be charged based on completion of infusion order preparation 506, the inventory and billing system 210 includes a crediting process. The crediting process can be triggered when infusion bags are returned to the pharmacy for disposal or re-entry into the pharmacy inventory management system.

The infusion system 210 includes a messages module 520 for communicating with entities throughout the patient care system 100. In particular, the messages module 520 sends text messages, audible indication enables, or both, to one or more electronic computing devices within the patient care system 100. The messages are sent in response to a status information output provided by the medication administration module or other infusion system modules within the patient care system 100. The messages relate to the status information output and, as such, provide alerts, alarms, reminders, or other messages appropriate in assisting the clinician with medication administration.

For example, when a physician enters a new order, messaging appears in the pharmacy to alert the pharmacists that an infusion order requires authorization. Likewise, when infusion orders are appropriately authorized, the clinician 116 receives messaging on digital assistant 118 to alert the clinician 116 that the infusion order should be administered according to the infusion schedule 704. Overrides 566 may generate messages 520 for the physician and/or the pharmacy. The infusion system 100 can distinguish between system-wide and sub-system overrides in determining whether it is necessary to generate a message 520. Messaging 520 includes messages received and/or sent to the central system, the pharmacy, the physician, billing, and inventory.

The system can present clinicians 116 with personal computer display views. The personal computer display provides a view summarizing outstanding clinical problems for the clinician's patients. The clinician 116 can quickly retrieve detailed information for the patients. The system 100 can also produce an email or page to digital assistant 118, or other communication device, when certain critical patient conditions prevail.

FIG. 6 also depicts some of the communication paths that occur in patient care system 100. The highlighted communication paths are presented for ease in describing the infusion system 210. Those having ordinary skill in the art recognize that when patient care system 100 is practiced on a network the various functional blocks can communicate with each other via the paths highlighted in FIG. 6 and via alternate paths that are not shown in FIG. 6. Setting system parameters 502 includes communicating data related to the system parameters to infusion order creation 504, via path 522, and/or receiving data from infusion order creation 504 and providing data informing infusion order creation 504 of how the received data relates to the system parameters.

Infusion orders can be passed directly, via path 524, to infusion preparation 506. Infusion orders can also be passed to pharmacy authorization 508, via path 526 and/or to physician authorization, via path 528, before being sent to preparation 506. Path 530 highlights the delivery of the medication 124 from the preparation area to the treatment location 106. Delivery can be accomplished using medication treatment cart 132. Paths 532, 534, 536, and 538 highlight that inventory and billing 518 transactions can be tied to a variety of other functions such as, but not limited to, infusion order creation 504, preparation 506, medication administration 512, and modifications 514. Paths 572, 574, and 576 highlight that a larger number of functions and actors involved in patient care system 100 can generate and receive information via messages 520. Path 582 highlights that system defaults 544 can be created and/or modified by the pharmacist. And, path 580 highlights that information, such as infusion orders, is available to a variety of functional units throughout the system 100.

Figure 7:
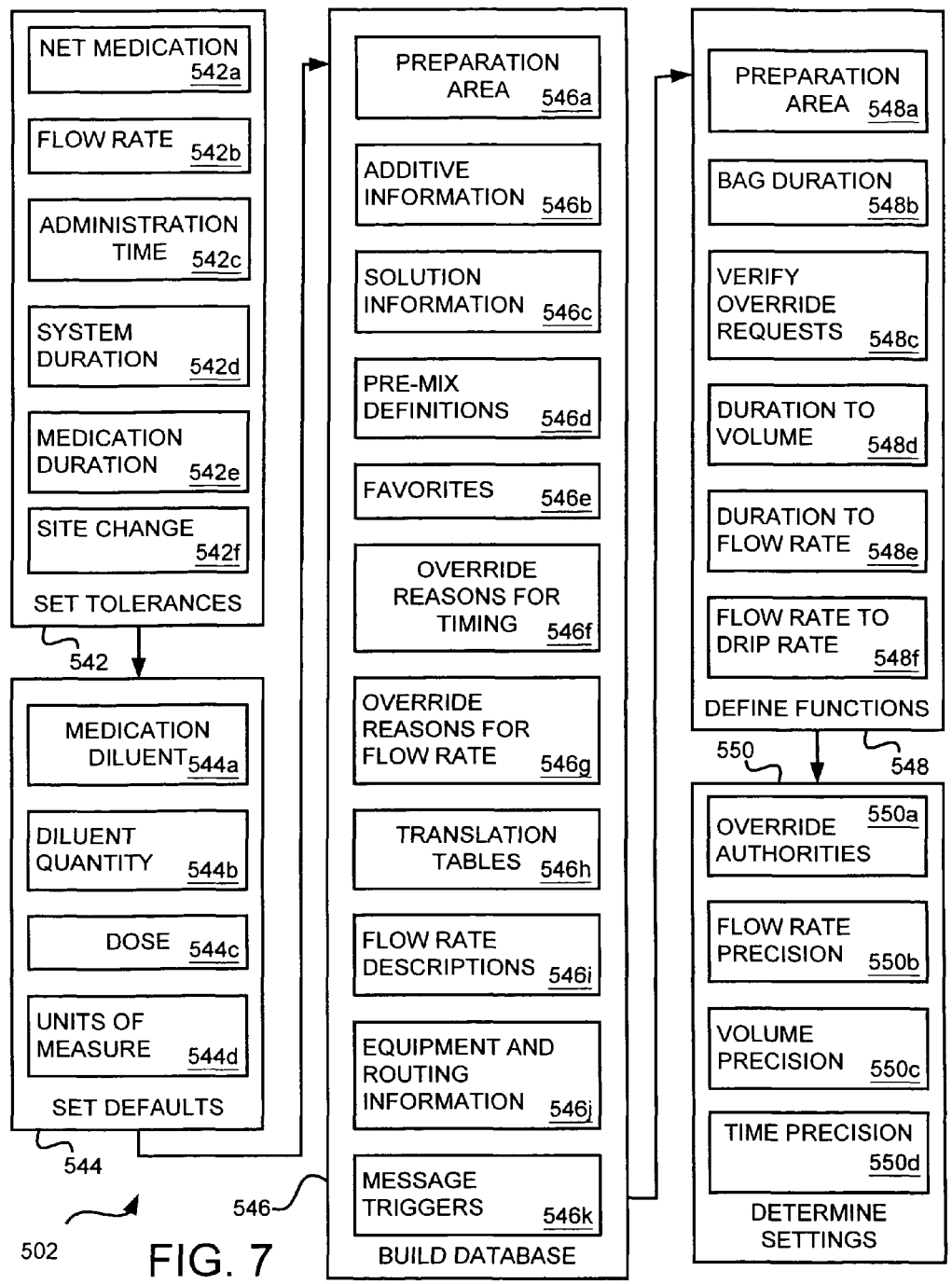
FIG. 7 is a block diagram showing functional components for the setting of infusion system parameters of FIG. 6.

FIG. 7 is a block diagram showing functional components for the setting of system parameters 502 of FIG. 6. Setting system parameters 502 includes, but is not limited to, setting tolerances 542, setting defaults 544, building databases 546, defining functions 548, and determining system settings 550. Tolerances 542 includes tolerances such as, but not limited to, net medication tolerances 542a, flow rate tolerances 542b, administration time tolerances 542c, administration system duration 542d, medication duration tolerances 542e, and site change tolerances 542f. The infusion system 210 can also include separate tolerances for order entry and modifications from the ordered tolerances. For example, separate tolerances can be identified such as, but not limited to, an administration system duration 542d, an order entry maximum infusion duration override availability setting, and an administration maximum infusion duration override availability setting.

A net medication tolerance 542a is a maximum concentration of a medication that is safe to administer to a patient. The infusion system 210 associates the net medication tolerances with medications. Net medication tolerances 542a can be defined in medication identification files in a medication database. During infusion order creation 504, the infusion system 210 can determine the flow rate 560e, the number of infusion bags required 562a for a specified period of time, the concentration of the primary ingredient in each infusion bag, the time period over which each infusion bag is to be administered, and the total volume of each infusion bag. Flow rates can be manually entered or adjusted by altering the final concentration or the duration of each infusion bag. In an embodiment, the infusion system 210 performs a net concentration check 564a (FIG. 8) to ensure the maximum concentration of the medication is not exceeded. However, if at any time while a clinician 116 is modifying the flow rate by adjusting the final concentration resulting in the final concentration of a solution exceeding the maximum concentration of the medication, the infusion system 210 sends a message 520 to the administering clinician. The administering clinician can be authorized override the net medication tolerance 542a. The infusion system 210 can require the clinician 116 to provide a reason for the override.

Infusion system 210 can include adjustable flow rate tolerances 542b and flow rate adjustment tolerances for administration. Flow rate tolerances 542b are optionally defined for all organizational levels of the patient care system 100. The tolerances 542b can be for the entire patient care system 100, or for sub-systems of the patient care system 100. For example, different flow rate tolerances 542b can apply to sub-systems such as, but not limited to, neonatal, pediatric, psychiatric, specific nursing units, and for specific patients. The flow rate tolerances 542b can be specified relative to the original ordered flow rate or relative to the immediately preceding flow rate. The clinician 116 can also specify a flow rate tolerance specific to a particular order.

The infusion system 210 can include a pre-defined indication of whether the administering clinician 116 is permitted to override the flow rate tolerance 542b without requiring a new order. This indication can apply to the entire patient care system 100, a sub-system, or an individual clinician 116.

The maximum infusion duration 542d can be separately definable for the various portions of the patient care system 100. The maximum infusion duration 542d can also be specific to a particular medication 124. A maximum infusion duration override 566 (FIG. 8) can be provided if it is permissible to override the maximum infusion duration 542d at the time of order entry. An administration maximum infusion duration override can be provided to set whether it is permissible to override the maximum infusion duration 542d at the time of administration and which group of users is allowed to do so. If it is permissible to override during order entry and/or administration, the infusion system 210 can define a subset of the clinicians 116 that have the authority to override the maximum infusion duration 542d.

Defaults 544 include defaults such as, but not limited to, medication diluent defaults 544a, diluent quantity defaults 544b, dose defaults 544c, and units of measure defaults 544d. Units of measurement (UOM) defaults 544d include the ability to specify the units of measurement that are most suitable for different portions of the patient care system 100. For example, medication can be measured in different units by physicians, administering clinicians, pharmacists, financial personnel, and medication screeners. The physician's UOM is generally a measurable value such as "mmol", "mEq", "ml", and/or "mg", as opposed to "vial" and/or "puff." The physician's UOM is used for tasks such as ordering and entering information 560.

The Administering clinician's UOM is generally a value that reflects the UOM the medication will be administered in, such as "puff", "tbsp", and "tab". The Administering clinician's UOM is used during medication administration 512. The Administering clinician's UOM can also appear on documentation such as administration reports, admixture fill and manufacturing work orders.

The pharmacy UOM is generally a value that reflects the physical form the medication is dispensed in such as "tab", "vial", "inhalator", and "jar". The pharmacy UOM is used in preparation 506 and in stocking and dispensing systems. The financial UOM is generally a value used to calculate the financial figures that appear on bills and invoices. The medication screening UOM is generally used when screening the medication.

Units of measurement defaults 544d can be specified using a check-box table where checkmarks are placed in a table correlating the various UOMs with the users of the UOMs. The infusion system 210 can use the same UOM for more one function. For example, the physician's UOM can be the same as the pharmacist's UOM. Setting defaults 544 include data necessary to coordinate the various UOMs. For example, UOM defaults 544d can include the multipliers and dividers necessary to create a one-to-one correspondence between the various UOMs. The UOM defaults 544b can be changed to suit the desires of the individual clinicians. However, the one-to-one correspondence should be maintained by the patient care system 100. The infusion system 210 can be designed to maintain a history of medication unit defaults.

The infusion system 210 can also include a medication measurement suffixes. The medication measurement suffixes can default during order entry. The medication measurement suffixes can be common units of measuring a medication and can include units related to patient characteristics such as body surface area and weight. Medication measurement suffixes can be designated per drug, per order type, per does, and per UOM.

Building database 546 includes building databases and/or portions of a single database such as, but not limited to, preparation area 546a, additive information 546b, solution 546c, pre-mix definitions 546d, favorites 546e, timing override reasons 546f, flow rate override reasons 546g, translation tables 546h, flow rate description 546i, equipment and routing information 546j, and message trigger 546k.

Figure 11:
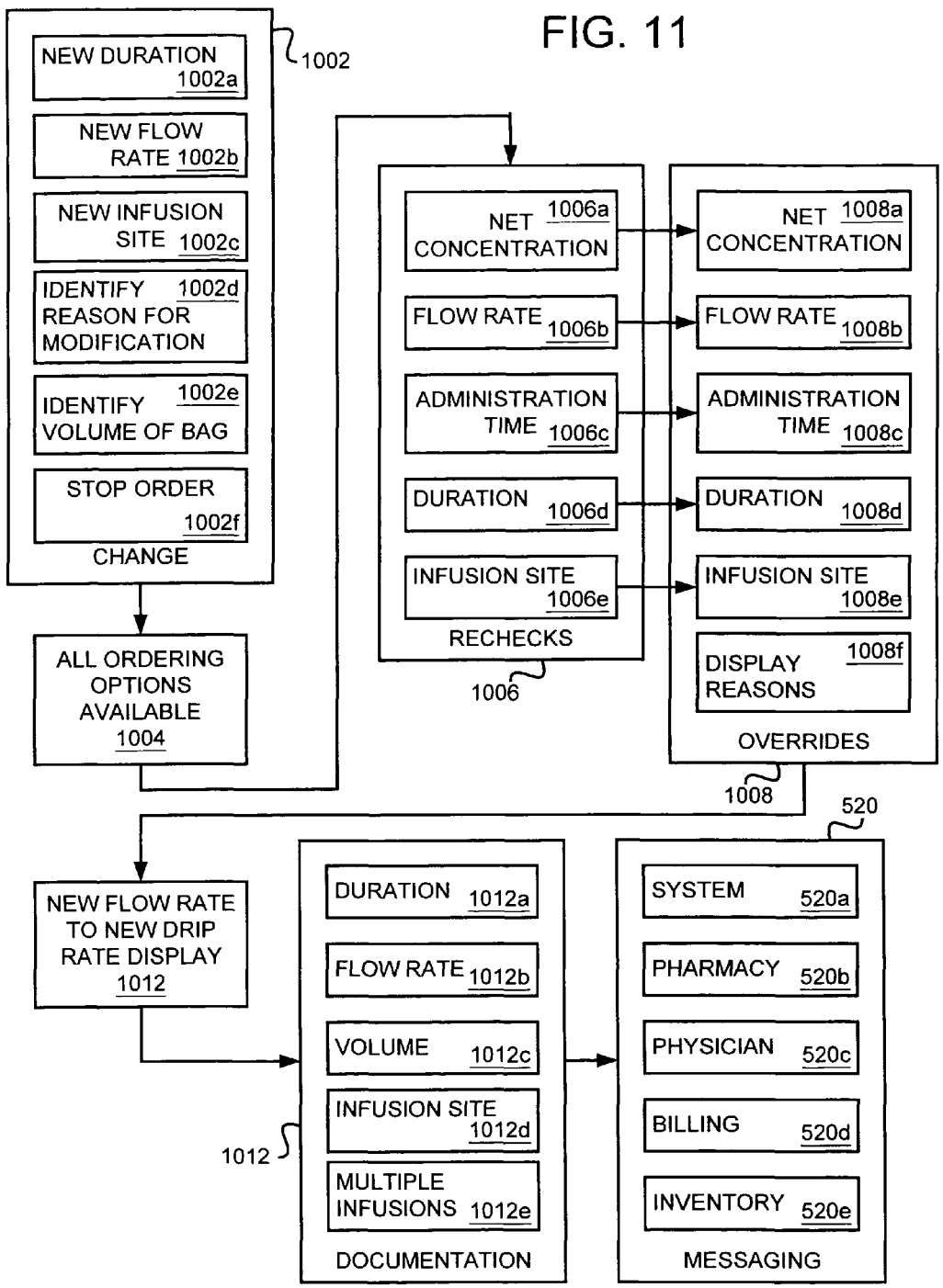

Timing override reasons 546f include displayable reasons for modifying the timing of infusion orders. For example, timing override reasons 546f can include a stylus selectable reason for digital assistant display 118a for administering an infusion order at a time other than the time specified in the original infusion order. If the clinician 116 administers a medication outside the ordered administration time tolerance 542c, the clinician 116 can be required to choose a reason code for the modification from displayed reasons 1008f (FIG. 11). An example of other reason codes includes, but is not limited to, PRN administration reason codes and codes for stopping an infusion.

Medications 124 and/or infusion orders can have flow rate tolerances, including system flow rate tolerances 542b. The infusion system 210 can include flow rate override reasons table 546g. Flow rate override reasons 546g are notations that the clinician 116 can choose from, and/or supply, if the clinician 116 needs to change the flow rate beyond the bounds defined by the flow rate tolerance 542b. The infusion system 210 can include a defined message trigger 546k indicating whether or not a message should be sent to the patient's physician if a clinician 116 overrides an order defined flow rate tolerance. The infusion system 210 can also include defined message triggers 546k indicating whether or not a message should be sent, and to whom, if a clinician 116 overrides a tolerance, such as flow rate tolerances 542b, defined at a level other than the order.

The infusion system 210 can include translation tables 546h such as, but not limited to, a flow rate translation table, a varying ingredient translation table, and varying flow rate translation table. Flow rate translation includes translating an infusion order into a flow rate defined by volume/time where the order is originally specified in any way such as, but not limited to, dosage/time with a particular concentration, volume per unit of weight/time, dosage per unit of body surface area/time, and total dosage and duration.

Varying ingredient translation includes translating a plurality of flow times of infusion orders with varying ingredients in separate infusion bags into the flow rate for the infusion bag currently being administered. Orders with varying ingredients include orders such as, but not limited to, sequencing orders. In sequencing orders, different bags have different ingredients and potentially different flow rates.

Varying flow rate translation includes translation of infusion orders with varying flow rates into the flow rate for the current solution being infused. Varying flow rate orders include orders such as, but not limited to, tapering dose orders and alternating dose orders.

The infusion system 210 can include predefined infusion flow rates 542b. The predefined infusion flow rates 542b can be associated with flow rate descriptions 546i to permit selection from a drop-down list as a shortcut from keying in the flow rate.

Defined functions 548 includes functions such as, but not limited to, preparation area function 548a, bag duration function 548b, verify override requests function 548c, duration to volume function 548d, duration to flow rate function 548e, and flow rate to drip rate function 548f. The infusion system 210 can include a duration-to-volume function 548d to determine the amount to be infused per the infusion order. Flow rate to drip rate function 548f uses information about the medical device 330 to convert flow rates to drip rates.

Determined settings 550 includes settings such as, but not limited to, override authorities 550a, flow rate precision 550b, volume precision 550c, and time precision 550d. The infusion system 210 can, if desired, determine the total volume of infusions and the flow rate(s) of the infusion order. If these numbers are determined, it is desired to round the calculated values to flow rate precisions 550b and volume precisions 550c that are comprehensible to clinicians 116 such as the physician, the pharmacist, and the nurse. Flow rate display precision 550b can be set to display the flow rate to a set number of decimal places. Various parts of the patient care system 100 can independently determine the precision for displayed flow rates. For example, the infusion system 210 can display to one decimal place for an adult treatment location, and to three decimal places for a neonatal treatment location. The flow rate precision 550b reflects the service in which the clinician's patient(s) are located. The flow rate(s) of the infusion order can be rounded to a system defined precision. The precision can be same for all infusion orders or be dependent on the patient's service.

Volume display precision 550c can similarly be set to display infusion volumes to a set number of decimal places. Settable time precision 550d can be used to calculate the administration duration period based on flow rate if the infusion is a single dose infusion or an intermittent infusion. The total volume of each infusion bag calculated is rounded according to the volume precision 550c. The administration time is rounded by the infusion system 210 according to the set time precision 550d. The time precision 550d can be the same for all infusion orders regardless of the patient's service or may be service specific.

FIG. 8 is a block diagram showing functional components for infusion order creation 504 of FIG. 6. Infusion order creation 504 includes functional blocks for creating infusion orders. Infusion order creation 504 includes entering information 560, calculations 562, checks 564, and overrides 568. Entering information 560 can include functions such as, but is not limited to, identifying the order type 560a, identifying the medications 560b, identifying the dose 560c, identifying the diluent 560d, identifying the flow rate 560e, and identifying the infusion site 560f.

Infusion order creation 504 is linked to infusion bag preparation 506, and infusion bag delivery (path 530), medication administration 512, and infusion order modifications 514. Infusion order types 560a include order types such as, but not limited to, single dosing, load dosing, intermittent dosing, and continuous. Continuous infusions include alternating infusions, sequencing infusions, tapering infusions, and titrating infusions. Upon selection of the first medication 560b in an infusion order, an infusion order type 560a form for the medication may default. The ordering clinician can have the option of selecting a different order type. The dose 560c and unit of measure 544d can also default. The unit of measure 544d can be correlated with the medication and/or the dose 544c. The infusion system 210 can include a default diluent, or several default diluents, for the medication. One default can be identified as a preferred diluent. A description can be associated with the diluent to assist the ordering clinician to decide which diluent to select. The diluent description can include a reference avoiding use of a particular diluent if a patient is hypertonic.

The infusion system 210 can also allow additional infusion order subtypes 560a based on the previously mentioned infusion order types. Additional infusion order subtypes 560a can include, but are not limited to, TPN infusion orders, chemotherapy continuous infusion orders, piggyback infusion orders, and large volume parenteral infusion orders. The infusion order subtypes can be accessed from different parts of the infusion system 210 allowing sorting and filtering of infusion orders according to the subtypes. A special label format for each infusion order subtype can also be defined to further customize infusion order subtype orders and associated pharmacy workflow.

When searching for a medication 114 during infusion order creation 504, the medication 114 can be flagged as additive and/or a solution to aid the clinician 116 in creating the infusion order. This designation can be made in a medication identification file.

Medication dose 560c can be determined in a number of ways such as, but not limited to, according to body weight, body surface area, and entered according to rate. When the flow rate is not entered, the infusion system 210 calculates the flow rate according to the dose and time period specified. The ordering clinician can specify the diluent 560d and its quantity. The pharmacy can provide a default for such parameters—see line 582 (FIG. 6). A check 564 can be performed to ensure the net concentration 564a for the medication 560b and the flow rate 564b are appropriate.

The infusion system 210 can identify and/or calculate flow rates 560e based on the patient's weight, body surface area, and/or a specified frequency and duration of therapy. The ordered flow rate 560e is checked 564b against the flow rate tolerances, such as system flow rate tolerance 542b. The net concentration of the medication 124 can be checked 564a against net concentration tolerances, such as the system net concentration tolerance 542a.

In an embodiment, flow rate 560e can also include displaying descriptions of default flow rates to facilitate the entering of orders. Flow rate 560e can reference flow rate descriptions database 546i.

Calculations 562 can include calculating the dose based on patient weight and/or height (possibly provided by ADT interface 310), the drug amount, diluent volume, concentration, or rate.

Calculations 562 can include, but are not limited to, calculating the flow rate, if not specified in the prescription, the bag quantity 562a or number of infusion bags required for a specified period of time, the time period over which each infusion bag is to be administered, and the total volume of each infusion and infusion bag based on the concentration of the ingredients in the solution. Flow rates, volume to be infused, and/or duration can be modified. If modified, the infusion system 210 automatically calculates dependent quantities, based on calculations, if the maximum dosage for the ingredients in the concentration would be exceeded as identified in the ingredient's medication file, the patient care infusion system 210 alerts the pharmacist and/or clinician 116 and can ask for a reason code for the adjustment.

Calculations 562 can include calculations such as, but not limited to, bag quantity calculations 562a, translation calculations 562b, duration to volume calculations 562c, and flow rate to drip rate calculations 562d. Checks 564 include a variety of checks that an infusion order can be subject to. The checks include checks such as, but not limited to, a net concentration check 564a, a flow rate check 564b, an administration time check 564c, a duration check 564c, and an infusion site check 564e. If an infusion order fails a check 564, the clinician 116 may be able to override the check. Overrides 568 can include overrides such as, but not limited to, a net concentration override 566a, a flow rate override 566b, an administration time override 566c, a duration override 566d, and an infusion site override 566e. Overrides 568 can generate messages 520 for the physician and/or the pharmacy. The infusion system 210 can distinguish between system-wide and subsystem overrides in determining whether it is necessary to generate a message 520.

Overrides can include an indication of whether clinicians have the authority to override a tolerance. For example, flow rate override 568b can provide an indication of whether the clinician entering the infusion order has the authority to override the system flow rate tolerance 542b. This indication can apply to the patient care system 100 or a sub-system. Duration override 568d can provide an indication of whether the clinician 116 entering the infusion order has the authority to override the system duration 542d. This indication can apply to the patient care system 100 or a sub-system.

Overrides 566 also include displaying of reasons for the override 568f. Reasons for the overrides 568f can be selected by the clinician 116 from drop-down menus.

The result of the infusion order creation 504 is an infusion order 702. Infusion order 702 can include an infusion schedule 704. The infusion system 210 can look ahead a period of time and generate the infusion schedule 704—so long as the infusion order 702 is active—for infusion bag filling for that time period, or longer if specified on demand. The ordering clinician is not required to specify an end-date for the infusion order. The infusion system 210 can include automatic scheduling of infusion bag delivery based on infusion system 210 defined tolerances 542.

Figure 9:
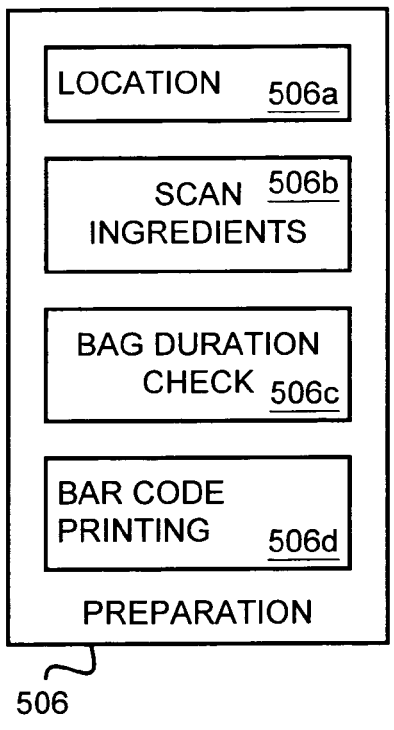
FIG. 9 is a block diagram showing functional components for the infusion order preparation of FIG. 6.

FIG. 9 is a block diagram showing functional components for infusion order preparation 506 of FIG. 6. Infusion preparation 506 includes functional blocks for preparing infusion order 702 (FIG. 8). Infusion preparation 506 can include, but is not limited to, determining preparation location 506a, scanning ingredients 506b, bag duration checking 506c, and bar code printing 506d for medication labels 124a. Bar code printing 506d can include the functions described above in reference to print label 326 (FIG. 4).

After infusion orders are entered into the infusion system 210, preparation instructions are routed to a preparation location. The preparation location depends upon the infusion system's 100 preparation program 506 and the infusion components. The infusion system 210 can include adjustable databases, such as preparation area database 546a that specify where the infusion order is to be prepared. The infusion order can be prepared in the pharmacy or in a remote location, such as on the floor or at the treatment location 106. The clinician 116 is guided through the preparation process, including bar code verification of ingredients, using event management information that can be displayed on digital assistant 118 or another device having a display.

The medication label 124a identifies the ingredients and ingredient concentrations. The medication label 124a can be printed in any location. The medication label 124a preferably includes bar code printing 506d. Bar code printing 506b can include printing a bar code label 124a for each infusion bag. The label 124a assists in ensuring that the correct medication is administered at the correct times and/or in the correct sequence. Alternating and sequencing infusion orders are particularly vulnerable to sequencing and timing errors. Bar code printing 506b can include printing a unique bar code label for every bag in infusion order 702. Bar code printing 506b can also include printing a bar code label 124a that uniquely identifies the combination of ingredients in an infusion bag and the concentration of those ingredients. The bar code for medication 124 can include a prefix, a suffix, and the national drug code (NCD). In an embodiment, the bar code can also include a lot and expiration date. Alternatively, a separate bar code can be provided to include the lot and expiration date.

Figure 10:
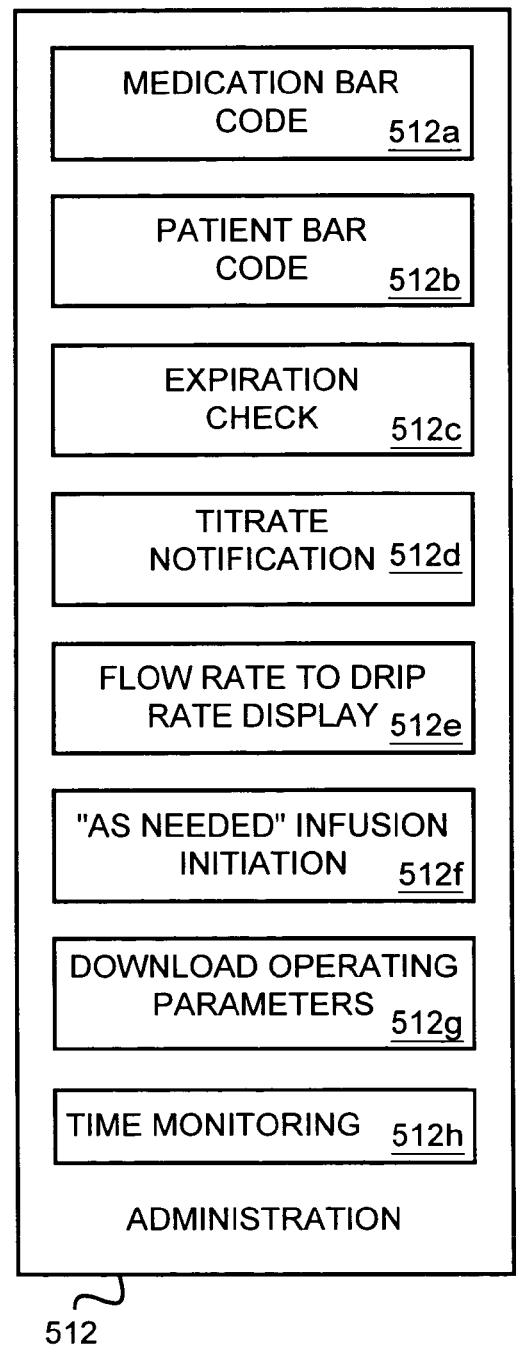
FIG. 10 is a block diagram showing functional components for the medication administration of FIG. 6; and, FIG. 11 is a block diagram showing functional components for infusion order documentation, infusion order modifications, and messaging of FIG. 6.

FIG. 10 is a block diagram showing functional components for medication administration 512 of FIG. 6. Medication administration 512 includes functional blocks that are used to administer the medication to patient 112. Medication administration 512 can include reading a medication bar code 512a, reading a patient bar code 512b, running an expiration check 512c, providing titrate notification 512d, providing a flow rate to drip rate display 512e, providing "as needed" infusion initiation 512f, downloading operating parameters 512g, and time monitoring 512h. The infusion system 210 can also translate orders that may have more than one flow rate, such as tapering and alternating orders, into the flow rate for the infusion bag currently being administered. The infusion system 210 can also translate orders having infusion bags with different ingredients, such as sequencing orders, into the flow rate for the infusion bag currently being administered.

Upon administering the medication 124, the clinician 116 scans the medication label 124a. The infusion system 210 includes scanning the bar coded label 24a when initiating the administration of the infusion order, when changing flow rates, changing bags, and/or stopping the infusion order. Infusion system 210 verifies that the infusion bag having the bar coded label should be administered at that time and is for patient 112. The history of the medication administration, including flow rates and volumes administered, can be captured and maintained. Some infusion orders require hanging of an infusion bag with the intent of only a partial, specific amount of the infusion bag to be administered. The infusion system 210 allows a clinician 116 to order an amount of an infusion bag to be administered. Most infusion pumps have the ability to define the volume to be administered or the flow rate and time period. Once this time has elapsed, the infusion pump will automatically prevent further administration. Infusion system 210, as a reminder to the administering clinician, provides a message on the medication label 114a that it is to be partially administered and the appropriate volume to be administered.

Flow rate to drip rate display 512e uses data generated by flow rate to drip rate functions 548f to provide the administering clinician with drip rates for the current infusion bag. During medication administration 512, the clinician 116 can check on the flow rate and other operating parameters using the digital assistant 118. Flow rate modifications 1002b (FIG. 11) are communicated in real-time.

The infusion system 210 can include PRN or "as needed" infusion initiation 512f. "As needed" infusion initiation 512 causes the creation of a new active order and the preparation of the PRN medication. This option can include prompting the clinician 116 to select a PRN infusion from a list of anticipatory PRN orders placed for the patient and defaulting the requested infusion bags to one. The clinician 116 can have the authority to modify the requested quantity of infusion bags.

Downloading of operating parameters 512g can include determining whether the patient identifier associated with the medical treatment and/or the patient identifier retrieved from the wristband 112a, is the same as the patient identifier associated with the medical treatment at the central location. The determination often is made by the first computer, for example, the pharmacy computer 104a. If the infusion system 210 determines the various patient identifiers are not the same, the system can generate an alarm message 520. If the infusion system 210 determines the various patient identifiers are the same, the infusion system 210 can download the operating parameters directly to the medical device 332. The infusion system 210 can send the operating parameters to a medical device 332, such as infusion pump 120.

One benefit of the system program 210 is that the operating parameters for the medical device 332 do not have to pass through digital assistant 118, or any other computer in the remote location, prior to the operating parameters being available to program the medical device 332. Bypassing computers at the remote location eliminates a potential source of errors in administering medication 124 to a patient 112. The operating parameters for the medical device 332 can be sent "directly" to the medical device 332 assuming the various verifications are achieved. In this context, "directly" meaning that the operating parameters can be sent to the medical device without passing through the digital assistant 118, or any other computer in the remote location.

In another embodiment, the infusion system 210 can include an additional block (not shown) where the central computer accepts a second medication identifier. The clinician 116 at the remote location can enter the second medication identifier. The second medication identifier can be a revised first medication identifier. For example, the second medication identifier can be part of the prescription or electronic physician order entry that is the source for the first patient ID and the operating parameters. The infusion system 210 can then confirm the first and second medication IDs are equivalent prior to sending the operating parameters to the medical device. The second medication ID can be replaced by a revised first medication ID between the time the prescription is entered and the time the medication 124 arrives at the treatment location 106. The infusion system 210 will then sound an alarm if the second medication identifier is not equivalent to the first medication identifier that was included in the medication label 124a. In a further embodiment, the infusion system 210 can include an additional block (not shown) where the operating parameter is used to program the medical device 332.

Various blocks of the infusion system 210, such as block 512, can include displaying treatment information on the digital assistant 118. This can include displaying information that mirrors the information on display 120c of infusion pump 120. The information on display 120c of infusion pump 120 can be supplemented with information about the patient 112, the patient location, and the infusion order. This information can include information regarding multiple channels of infusion pump 120. The displayed information can include information such as, but not limited to, personality, prompt line, status line, operating icons and pump head display. Operating icons include falling drop, stop sign, flow check piggyback, Guardian, and delay start. The pump head display includes information such as the drug label and the infusion rate. Those having ordinary skill in the art are familiar with the displayed information and operating icons described above.

The infusion system 210 time monitoring 512h calculates the time remaining for an order to be completed and the volume of an infusion order that remains to be administered. When the clinician 116 uses the infusion system 210 to administer the infusion order, to make flow rate changes, and to check on the status of an infusion, the infusion system 210 calculates time and volume remaining to be administered and indicates if the calculation indicates a partial bag will be used. For example, on the last bag of an order that is to be stopped before the full volume is administered, and/or on a bag within an order that must be changed before the full volume is administered, the clinician 116 is alerted on digital assistant 118 and/or cart 132. The alert can include a message such as "Please only administer 150 ml."

Time monitoring 512h includes tracking any modifications made to the flow rate using bar code scanning. The pharmacy is alerted in real time to adjust the preparation 506 of the next required infusion bag according to the modification. Monitoring of preparation 506 and medication administration 512 allows for a just-in-time delivery of medication 124. Just-in-time delivery reduces wastage attributed to discontinued or changed infusion orders. Monitoring also ensures patient 112 safety.

For titrate PRN orders, the clinician 116 is automatically notified of required flow rate changes if the titration conditions in the order indicate that the flow rate must be changed. The infusion system 210 includes defined functions for calculating a conversion of flow rates to drip rates 548f. The infusion system 210 defined values can be adjustable. The infusion system 210 can include automatic translation of flow rate to drip rate 548f to assist the clinician 116 during administration of the treatment.

FIG. 11 is a block diagram showing functional components for infusion order documentation 1012, and the infusion order modifications 514 and messaging 520 of FIG. 6. Modifications 514 include functional blocks used to modify existing infusion orders. Modification 514 can also be viewed as creating new orders to replace existing infusion orders. Modification 514 can include modification changes 1002, generally all ordering options for new orders 1004 are available, rechecks 1006, recheck overrides 1008, and new flow rate to new drip rate display 1010. Infusion order modifications often lead to documentation 1012 and messaging 520. Modifications 514 include the functions described in reference to prescription modification module 336 (FIG. 4). However, modifications 514 are also accessible from other portions of the patient care system 100 such as, but not limited to, prescription entry 324, prescription activation 306, and prescription authorization 308.

Modifications 514 include modifying the duration 1002a, modifying the flow rate 1002b, using a new infusion site 1002c, identifying reasons for modifications 1002d, identifying the volume of an infusion bag 1002e, and processing stop orders 1002f. Clinicians 116 can also change an infusion rate without an order if the patient 112 is complaining of discomfort or to facilitate fluid balance, such as when the patient 112 is vomiting.

Modification changes 1002 include identifying a new duration 1002a, identifying a new flow rate 1002b, identifying a new infusion site 1002c, identifying a reason for a modification 1002d, identifying the volume remaining in the infusion bag 1002e, and stop orders 516. The ordering options available during initial infusion order creation 504 are generally available for modifying the infusion order. Ordering options available during initial infusion order creation 504 include those shown in FIG. 8. Rechecks 1006 and recheck overrides 1008 are analogous to checks 564 and overrides 566 that are described in reference to FIG. 8. New flow rate to new flow rate display 1010 assists the clinician and minimizes the possibility of errors during medication administration 512. The modified infusion order can lead to a modified infusion schedule.

Flow rates are frequently modified at the treatment location 106 for reasons such as to catch-up without changing the schedule for preparation when the infusion has been inadvertently stopped for a short time period. Such modifications may not require new infusion schedule 704 to be communicated to the pharmacy. In other cases, the new schedule 704 should be communicated to the pharmacy or other preparation staff. Flow rate modifications 1002b triggers infusion order scheduling changes and/or messages 520 for appropriate clinicians 116.

When a clinician 116 enters a flow rate modification 1002b into the infusion system 210 at treatment location 106, the clinician 106 can also elect to have the infusion schedule 704 recalculated and sent to the pharmacy. The clinician 116 has the option of requesting new medication labels 124a to be printed by bar code printing 506d module. The new medication labels 124a include data reflecting the new information for any of the previously prepared infusion bags.

The infusion system 210 and/or the clinician can request a modification to the infusion site 1002c. The site can be selected from a list of anatomical representations on a computer screen.

The clinician 116 can be required to identify a reason for the modification 1002d. Reasons stored in databases such as, but not limited to, override reasons for timing 546f and override reasons for flow rate 546g, can be displayed for easy identification by the clinician 116. There can be a separate hard-coded reason for physician ordered modifications. For physician ordered modifications, the clinician 116 can be requested to identify the physician.

Prior to implementing the modification, the volume remaining in the current infusion bag is identified 1002e. The clinician 116 can be offered the option of accepting a volume calculated from a displayed value of pre-modification flow rate and/or volume.

If desired, the current infusion can be stopped 1002f. If stopping the order is not required, for example the same infusion bag can be used with a new flow rate and/or a new medication added, the old flow rate can be identified and compared to the modified flow rate.

Any infusion bags that were previously prepared can be checked for expiration based on the new infusion schedule 704. When an infusion order is resumed following either a temporary stop or a hold order, the expiration check can be done regarding expiration of solutions that have already been prepared.

The new infusion schedule 704 is used to control the preparation 506 in the pharmacy or other preparation site. A system default 544 can be set for whether or not any prepared bags should be credited to the patient 112, through the billing interface 312, and whether or not they should be credited to inventory.

Infusion order changes 1002 include all ordering options available 1004 for new orders. The modified flow rate can be rechecked 1006 for rules and tolerances such as, but not limited to, net concentration 1006a, flow rate 1006b, administration time 1006c, duration 1006e, and infusion site 1006f. Overrides 1008 can be available for modifications that are outside of tolerances. The infusion system 210 can display reasons 1008f for overrides and for administering medications at times other than that specified in the original order. The clinician 116 can be required to identify a reason for the modification.

The infusion system 210 can offer the clinician 116 a display indicating the modified drip rate associated with the modified flow rate 1012. The displayed information can be calculated by the flow rate to drip rate 548f defined function. The infusion system 210 can also be provided with descriptions of typical infusion tubing used within the infusion system 210 for use in calculating drip rates.

A modification results in the infusion system 210 validating the expiration of the infusion bag and providing a message to the clinician 116 if the infusion bag expires prior to the completion of the order. The message can request that the clinician 116 contact the pharmacy. The validation of the expiration of the infusion bag for solutions such as, but not limited to, premixed solutions and solutions manufactured outside of the infusion system 210, may include parsing the scan code.

Flow rate override 1008b can provide an indication of whether the clinician 116 modifying the infusion order has the authority to override the ordered override without requiring approval for a new infusion order. This indication can apply to the patient care system 100 or a sub-system.

Documentation 1012 captures infusion order information in real-time. Documentation includes documenting multiple infusions being administered at the same time and infusion modifications such as, but not limited to, duration changes 1002a, flow rate changes 1002b, volume changes 1012c, and infusion site changes 1002d.

The infusion system 210 can assist the clinician 116 in capturing all changes in flow rate as the changes are occurring. The clinician 116 can change the flow rate as called for in the order, such as to decrease a morphine infusion flow rate from 4 ml to 2 ml. Though the infusion system 210 may recognize the change as a new order, the infusion system 210 may be configured to avoid duplication so that the modified order does not result in the generation of a new bag.

Documentation 1012 includes the ability to document changes such as, but not limited to, an infusion that is stopped temporarily, discontinued, and/or restarted. The clinician 116 may stop infusion for a variety of reasons, such as the infusion site having been compromised, the infusion has been dislodged, and/or the infusion may be heparin/saline locked to facilitate the movement of patient 112. The infusion can be resumed when a new site/infusion has been reestablished. However the length of time this may take is variable and is generally recorded by the infusion system 210.

Government regulations often require tracking of every step in the process of infusion administration. Infusion system 210 allows the administering clinician 116 to document flow rate modifications on a digital assistant 118, or other computer device, by scanning the medication label 124a and adjusting the flow rate 1002a based on a tolerance, such as a tolerance created by set tolerance 542. A flow rate modification 1002b corresponds in real time with the associated pharmacy's infusion schedule 704 to ensure just-in-time inventory management of infusion bags to the patient treatment area 106. Documentation 1012 may allow order backdating under some circumstances.

The infusion system 210 includes the ability to document the infusion site 1012d and multiple infusions 1012e for multiple infusion sites. In many situations a patient 112 can have multiple medications 124 and "y-ed" infusions so that the some infusions are running into one site and other infusions are infusing into another site. For example, morphine infusion, antibiotics and normal saline infused into the right arm (site 1) and TPN and $\frac{2}{3}$ & $\frac{1}{3}$ running into a double lumen CVL (site 2). The infusion system 210 allows clinician 116 to document which site the various fluids are infusing through. In treatment locations 106, such as intensive care units, many more than two infusions may be running into one line or one lumen. Clinicians 116 are able to indicate which lumen of a CVL the infusion or medication is running into.

The infusion system 210 includes the ability to document the site location 1012d for infusions and any site location changes. Infusion sites are frequently changed due to occlusions or policy. Therefore, clinicians 116 must document a change in the site location if an infusion becomes dislodged and was subsequently restarted.

The infusion system provides for centralized device configuration. Operating parameters for medical devices 332, such as infusion pump 120, often include defaults and/or tolerances. The defaults and/or tolerances can reside in the infusion system 210, for example flow rate tolerance 542b, and/or in a memory associated with the device 332. For example, infusion pumps 120 can include a database having a table of medications having associated flow rate tolerances. If the clinician 116 enters a flow rate that is beyond the associated flow rate tolerance, the clinician 116 is warned and then can be allowed to proceed—or prohibited from proceeding. Devices 332 such as heart rate monitors can also have configurable tolerances for alerts. In addition to alerts, many other characteristics can typically be configured for devices 332 such as: network name, IP address, polling frequency, and colors. The infusion system 210 includes configuring medical devices 332 individually or in groups from one or more central computers.

System configuration parameters can be defined for a first type of medical device. The system configuration parameters are sent and accepted by the first type of device unless the particular first type of device has more specific configuration parameters that apply to that particular first type of device. For example, a first plurality of a first type medical device can be located at general care treatment locations. A second plurality of the first type of medical device can be located at an intensive care treatment location. The general care treatment location may not have specific configuration parameters while the intensive care treatment location does have specific treatment parameters. System configuration parameters will apply to all of the first type of medical devices throughout the infusion system 210, i.e. the devices in the general care treatment locations, unless specific configuration parameters apply, e.g. the intensive care treatment location.

For each type of device, specific configuration parameters that apply to all devices of that type across a particular grouping of the devices override the system configuration parameters if a particular device belongs to the group having such a definition, unless the specific configuration parameters are overridden at an even more specific level within the infusion system 210. The groups might be defined as a clinical service, a nursing unit, and/or a combination of service and nursing unit.

For each type of device, the user can define sets of configuration parameters that apply to all devices of that type being used for operations with specified ranges of attributes that override any other definition. In a hospital the operations might consist of infusion orders and the attributes might include patient weight, drug, patient disease state, and patient acuity.

Devices can be identified as part of a general group, a specific group, and/or to be associated with a particular patient by including the device address in a table in a database. General or specific configuration parameters can then be sent to the device according to the identification of the device. The specific configuration parameters can then be read back to the infusion system 210 and compared to the originally sent configuration parameters to verify the original configuration parameters were correctly received by the device 332. If the configuration parameters were not correctly received, the infusion system 210 can provide a message 520 identifying the discrepancies or the communication failure.

The infusion system 210 can detect changes to configuration parameters made at the device, rather than through a central computer, and send a message and/or alert 520. The infusion system 210 can also poll the devices to verify their configuration parameters. If system and/or specific configuration parameters change, the changes can be propagated to all devices 332 identified in the system as belonging to the group according to the groupings identified in the infusion system 210.

Throughout this document and the related claims, "central location" and "remote location" are relative terms to each other. A "remote location" is any location where a patient is receiving treatment through a controlled medical device, such as a patient treatment location 106 where patient 112 is receiving treatment through an infusion pump 120. "Central location" is any location, other than the remote location, where parameters for operating the medical device are accessible such as, but not limited to, the location of the pharmacy computer 104 and the central system 108. In a typical arrangement, several remote locations, such as treatment location 106, are in communication with a central location.

In an embodiment, the system can automatically provide clinicians with information associated with one or more medications via pop-up windows. Preferably, a medication table is entered into the central database 108b. The medication table can include the generic name of one or more medications, and any trade names associated therewith. Linked to each medication within the medication table are respective messages for display via pop-up windows. The messages can be defined by the health care facility, or predefined by the system provider.

Preferably, the messages associated with each medication pertain to: 1) hazards associated with the medication, such as in handling or exposure thereto; 2) how the medication is to be administered by a clinician; and 3) physician reference information about medication.

The pop-up windows are displayed when a medication is selected or entered into a computing device such as: when the medication is being ordered by a physician via the CPOE; when the medication is being processed by the pharmacy or the like; and when the medication is being administered to a patient by a clinician. In an embodiment, when the selection or entry of a medication has been made on a computing device at a remote location, the database within the central system 108 is accessed wherein at least one of the pop-up window messages associated with the medication is provided to the remote computing device for display to the clinician.

Preferably, at least one of the pop-up window messages associated with a medication is provided for display upon the initiation of a specific step in the medication order, process, and administration procedure. For instance, upon entry of a medication order into a computing device such as the CPOE, a pop-up window is displayed with a message regarding physician reference information about the medication and, in an embodiment, another pop-up window can be displayed regarding hazards associated with the medication. Then, upon processing of the order by a pharmacy or the like, one or more pop-up windows are displayed on a computing device within the pharmacy 104 for providing general information about the medication, and possible hazards associated therewith. Next, when the order is being administered by a clinician, one or more pop-up windows are displayed on a computing device associated with the clinician (i.e., handheld 118) for providing information about administration of the medication, and, in an embodiment, possible hazards associated with the medication such as how the medication is to be handled.

Preferably, the pop-up windows displayed on a computing device are specific to the step in the medication order, process, and administration procedure that is being carried out by a clinician. For instance, the pop-up window containing physician reference information is preferably not displayed to the nurse, via handheld device 108. Nevertheless, in an embodiment, the user or hospital can define when, and if, a pop-up window should be displayed when a medication is selected or entered into a specific computing device.

It is also preferred that the pharmacy define when, and if, a pop-up window is to be displayed. For instance, pop-up windows are preferably not displayed for common medications. Instead, pop-up windows are preferably displayed for medications wherein the pharmacy or healthcare facility believes that the additional information within the pop-up window will assist in the ordering, preparing, or administration of the medication.

A method of administering a medication with the infusion system 210 is described below. The method includes the ability to modify the infusion order. The modifications include modifications to the flow rate, the infusion site, temporary stops to the infusion, restarting the infusion, and hanging a new medication 124 container. The method includes: scanning a bar code associated with the patient 512b; scanning a bar code associated with the medication 512a; if the infusion is an admixture, validating the expiration 512c; selecting a reason for the modification 1002d; and recording the remaining volume of the infusion bag or accepting the value calculated from the previous volume and flow rate 1002e. The validation of the expiration 512c of the infusion bag can include the use of an admixture table and/or a bar code.

The reason for the modification may come from a defined table 546g. The reason for the modification may also include a hard-coded value for physician-ordered changes. When the hard-coded value is selected, the clinician 116 is prompted to select the physician from a list of physicians. The attending physician can be the default in the list of physicians.

There may be a quick select feature to halt the administration of the medication 124, for example stop order 12002f. If the quick select is not chosen, the following steps can be included: recording the flow rate and/or accepting the previous value for the flow rate—the previous value is displayed on the digital assistant display 118a, the infusion pump display 120c, and/or the medical cart 132; comparing the previous flow rate to the ordered flow rate—this comparison can be accomplished by using infusion system 210 or subsystem rules and tolerances; displaying appropriate messages; conversions between flow rates and drip rates can be displayed 1012—the conversions can be calculated based on infusion system 210 defined drip-rate conversion tables 548f. The infusion system 210 typically uses descriptions based on the tubing used to make it easy for the clinician 116 to select the correct drip rate conversion.

Changing the flow rate triggers the infusion system 210 to validate the expiration of the infusion bag(s) based on scheduled flow rate. If the solution expires before or during the administration, send a message to the clinician 116, such as "This solution will expire during the scheduled administration period. Please contact the pharmacy." If it is a premixed infusion bag and/or a customized infusion bag, validate the expiration by parsing the scan code, if possible. Accept the previous infusion site or select a new infusion site location from a list or a graphical anatomical representation. Then recalculate the schedule 704 to implement pharmacy restocking.

Infusion system 210 can include biometrics for identifying patients and clinicians 116. Prior to allowing a clinician 116 to access the infusion system 210, the infusion system 210 accesses information related to the identity of the clinician 116. The infusion system 210 can identify the clinician by using a device, such as a bar code reader, to read the clinicians' badge 116a. The system can also use biometrics to positively identify the clinician 116, to assure the clinician is an authorized user of the system, and to determine whether the clinician 1176 has authority to access portions of the infusion system 210. The infusion system 210 can require a combination of the clinician badge 116a, or other key, and a verified biometric match in order to grant the clinician access to the infusion system 210. The system can also be configured to terminate access to the infusion system 210 when the clinician badge 116a is removed from the vicinity of the device used to read the clinician badge 116a, or other key.

Biometrics is the technology and science of statistically analyzing measured biological data. One field of biometrics is that of determining unique physical characteristics, such as fingerprints. Biometrics makes it possible to identify individuals to digital systems, such as infusion system 210. A digital persona is created that makes transactions and interactions more convenient and secure. Biometric features for identification include features such as, but not limited to, fingerprint, face, iris and retina scanning, and voice identification. Biometric devices include a scanning or reading device, software to convert the scanned information into a digital format, and a memory to store the biometric information for comparison with a stored record. Software identifies specific matched points of data that have been processed with an algorithm and compares the data. Unlike passwords, PIN codes, and smartcards, the infusion system 210 biometrics cannot be lost, forgotten, or stolen.

The biometric scanner can be associated with the device for reading the clinician's badge 116a. For example, the biometric scanner can be a thumb print reader on the handle of a bar code reader. In other embodiments, the biometric scanner and an electronic key reader can be located on the portable medicine cart and/or the medical device. When the clinician 116 places the electronic key within a specified distance of the medical device, a processor will know the specific individual electronic biometric identification file it should expect. The infusion system 210 preferably prompts the clinician 116 to scan his biometric information. The biometric information is entered into the infusion system 210 with some type of biometric reading or scanning device. A one-to-one comparison is made between the scanned biometric information and the previously stored specific individual electronic biometric identification file. This one-to-one identity comparison is more efficient than comparing one-to-many identity files because it does not require searching an entire clinician database for a match. Instead, only one specific comparison is made. If there is a match, then the clinician 116 is granted access to the medical device 332. If there is no match, the clinician 116 is denied access.

In another embodiment, after the infusion system 210 grants access to the clinician 116, the infusion system 210 terminates that access when the electronic key is removed from the biometric scanner, or the vicinity of the biometric scanner. The vicinity within which the electronic key must be kept can be predetermined and/or may be a variable and programmable infusion system 210 parameter.

In one embodiment, the infusion system 210 includes an encrypted digital fingerprint template, a clinician's name, a login name, and a password. One technology for implementing the clinician identifier includes "IBUTTON 400" technology from Dallas Semiconductor technology. The infusion system 210 can be activated when the clinician places a finger on a fingerprint scanner. If the infusion system 210 finds a match, the infusion system 210 can request the clinician 116 login to the infusion system 210. If the infusion system 210 does not find a biometric match, the system does not allow the clinician 116 to access the infusion system 210.

In another embodiment, the database storing biometric information can be kept in the central system 108, the pharmacy computer 104, and/or the treatment location 106. At the treatment location 106, the database can be maintained in the portable cart, the digital assistant 118, and/or the medical device 332. Such distributed databases allow access to remote devices even if the network 102 is unable to communicate between the various locations. When network 102 communication is reestablished, the remote and central databases can be synchronized with any information modified at the other location so that both infusion system 210 databases are properly updated.

The infusion system 210 provides a closed loop infusion therapy management system. The closed loop begins with a clinician 116 order. Among other methods, the clinician 116 can enter the order through digital assistant 118 and/or medical treatment cart 132. The order is then available in real-time for pharmacy authorization 508 and physician authorization 510. The order is available in real-time as an electronic medication administration record (eMAR). The eMAR is available to the clinician 116 for infusion administration. The infusion system 210 automatically documents medication administration 512 and modifications 514 such as flow rate changes 1002b. Through the process of medication administration 512, the infusion system 210 simultaneously adjusts infusion system 210 and/or sub-system inventory and billing 518. The infusion system 210 also provides event management and decision support data. The infusion system 210 is device independent, meaning that it can be run on workstations, wireless tablets, and handheld digital assistants 100. The infusion system 210 generally runs in real time, however, batch processing and or messaging can be used to coordinate various stages of the infusion system 210 processes.

The closed loop infusion therapy management system includes infusion order entry 560, order preparation 506, and the availability of the status of the infusion. Infusion order entry 560 can be through a number of means such as, but not limited to, the prescription entry module 324, the prescription modification module 336, and the pharmacy interface 316. Computer screen 400 can be employed in entering the infusion order. The status of the infusion provides patient 112 specific usage of infusions and alerts the pharmacy of the need for additional infusion bags.

It should be emphasized that the above-described embodiments of the present invention, particularly, any "preferred" embodiments, are possible examples of implementations, merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and the present invention and protected by the following claims.

What is claimed is:

1. A system for reporting on integrity of a wireless communication link within a healthcare facility comprising:
   a module associated with a medication treatment application device, the module having a status information output responsive to a signal output generated by the medication treatment application device;
   a wireless remote device within the healthcare facility having a visual display and having a message indicator responsive to the status information output transmitted over the wireless communication link and representative of the signal generated by the medication treatment application device; and
   software installed on the wireless remote device, the software configured to report upon the integrity of the wireless communication link by:
   (i) sending a signal to the wireless communication link,
   (ii) waiting a predetermined amount of time for a response to the signal sent to the wireless communication link,
   (iii) generating a time-out output that indicates loss of the wireless communication link when the response is not received within the predetermined amount of time; and
   (iv) providing on the visual display at least one of (a) an icon responsive to the time-out output or (b) a pop-up window in response to the time-out output.

2. The system of claim 1 wherein the association between the module and the medication treatment application device results in at least some data within the status information output passing through the module.

3. The system of claim 1 wherein the medication treatment application device is an infusion pump for administering an infusion to a patient.

4. The system of claim 1 wherein the output generated by the medication treatment device includes data related to an alarm condition.

5. The system of claim 1 wherein the output generated by the medication treatment device includes data related to an alert condition.

6. The system of claim 1 wherein the output generated by the medication treatment device includes data related to an infusion volume rate.

7. The system of claim 1 wherein the output generated by the medication treatment device includes data related to time remaining before an infusion bag is emptied.

8. The system of claim 1 wherein the wireless remote device is a personal digital assistant.

9. The system of claim 1 wherein the wireless communication link operates within a radio frequency.

10. The system of claim 9 wherein the radio frequency is within the 2.4 gigahertz band.

11. The system of claim 9 wherein the radio frequency is within the 2.45 gigahertz band.

12. The system of claim 9 wherein the radio frequency is within the 5 gigahertz band.

13. The system of claim 1 wherein the wireless remote device includes an audible alarm.

14. The system of claim 13 wherein the audible alarm produces an audible sound in response to the time-out output.

15. A method for reporting on integrity of a wireless communication link within a healthcare facility comprising the steps of:
   generating a status information output responsive to a signal output generated by a medication treatment application device;
   operating a message indicator in response to the status information output transmitted over a wireless communication link and representative of the signal generated by the medication treatment application device; and
   installing software on a wireless remote device that is configured to report upon the integrity of the wireless communication link by: (i) sending a signal to the wireless communication link, (ii) waiting a predetermined amount of time for a response to the signal sent to the wireless communication link, (iii) generating a time-out output that indicates loss of the wireless communication link when the response is not received within the predetermined amount of time, and (iv) in response to the time-out output, performing at least one of (a) modifying an icon on a visual display of the wireless remote device or (b) generating a pop-up window on the visual display of the wireless remote device.

16. The method of claim 15 further comprising the step of passing at least some data within the status information output through a module associated with the medication treatment application device.

17. The method of claim 15 further comprising the step of administering an infusion to a patient with the medication treatment application device.

18. The method of claim 15 further comprising the step of including data related to an alarm condition within the signal output generated by the medication treatment device.

19. The method of claim 15 further comprising the step of including data related to an alert condition within the signal output generated by the medication treatment device.

20. The method of claim 15 further comprising the step of including data related to an infusion volume rate within the signal output generated by the medication treatment device.

21. The method of claim 15 further comprising the step of including data related to time remaining before an infusion bag is emptied within the signal output generated by the medication treatment device.

22. The method of claim 15 further comprising the step of operating the wireless communication link within a radio frequency.

23. The method of claim 15 further comprising the step of operating the wireless communication link within a radio frequency band of 2.4 gigahertz.

24. The method of claim 15 further comprising the step of operating the wireless communication link within a radio frequency band of 2.45 gigahertz.

25. The method of claim 15 further comprising the step of operating the wireless communication link within a radio frequency band of 5 gigahertz.

26. The method of claim 15 further comprising the step of generating an audible sound in response to the time-out output.

27. The method of claim 15 further comprising the step of generating a notification on a the wireless remote device in response to the time-out output.

28. A method for reporting on integrity of a wireless communication link within a healthcare facility comprising the steps of:
providing for generating a status information output responsive to a signal output generated by a medication treatment application device;
providing for operating a message indicator in response to the status information output transmitted over a wireless communication link and representative of the signal generated by the medication treatment application device; and
providing for the installation of software on a wireless remote device that is configured to report upon the integrity of the wireless communication link by: (i) sending a signal to the wireless communication link (ii) waiting a predetermined amount of time for a response to the signal sent to the wireless communication link, (iii) generating a time-out output that indicates loss of the wireless communication link when the response is not received within the predetermined amount of time, and (iv) in response to the time-out output, causing at least one of (a) an icon or (b) a pop-up window to appear on a visual display of the wireless remote device.

29. The method of claim 28 further comprising the step of providing for passing at least some data within the status information output through a module associated with the medication treatment application device.

30. The method of claim 28 further comprising the step of providing for administering an infusion to a patient with the medication treatment application device.

31. The method of claim 28 further comprising the step of providing for including data related to an alarm condition within the signal output generated by the medication treatment device.

32. The method of claim 28 further comprising the step of providing for including data related to an alert condition within the signal output generated by the medication treatment device.

33. The method of claim 28 further comprising the step of providing for including data related to an infusion volume rate within the signal output generated by the medication treatment device.

34. The method of claim 28 further comprising the step of providing for including data related to time remaining before an infusion bag is emptied within the signal output generated by the medication treatment device.

35. The method of claim 28 further comprising the step of providing for causing a personal digital assistant to generate an audible sound in response to the time-out output.

36. The method of claim 28 further comprising the step of providing for causing a personal digital assistant to generate a notification on the visual display of the wireless remote device in response to the time-out output.

37. A system for reporting on integrity of a wireless communication link within a healthcare facility comprising:
a wireless remote device within the healthcare facility having a visual display responsive to status information transmitted over a wireless communication link, the status information responsive to a signal output generated by an infusion pump; and
software installed on the wireless remote device, the software configured to report upon the integrity of the wireless communication link by:
(i) sending a signal to the wireless communication link;
(ii) waiting a predetermined amount of time for a response to the signal sent to the wireless communication link,
(iii) generating a time-out output that indicates loss of the wireless communication link when the response is not received within the predetermined amount of time, wherein the time-out output indicates loss of the wireless remote device to receive the status information transmitted over the wireless communication link, and wherein an icon responsive to the time-out output is provided on the visual display, and
(iv) providing on the visual display at least one of (a) an icon responsive to the time-out output or (b) a pop-up window in response to the time-out output.

38. The system of claim 37 wherein the signal output generated by the infusion pump includes data related to an alarm condition.

39. The system of claim 37 wherein the signal output generated by the infusion pump includes data related to an alert condition.

40. The system of claim 37 wherein the signal output generated by the infusion pump includes data related to an infusion volume rate.

41. The system of claim 37 wherein the signal output generated by the infusion pump device includes data related to time remaining before an infusion bag is emptied.

42. The system of claim 37 wherein the wireless remote device is a personal digital assistant.

43. The system of claim 37 wherein the wireless communication link operates within a radio frequency.

44. The system of claim 43 wherein the radio frequency is within the 2.4 gigahertz band.

45. The system of claim 43 wherein the radio frequency is within the 2.45 gigahertz band.

46. The system of claim 43 wherein the radio frequency is within the 5 gigahertz band.

* * * * *